(12) United States Patent
Sohn

(10) Patent No.: US 11,612,627 B2
(45) Date of Patent: Mar. 28, 2023

(54) METHOD FOR PREVENTING OR TREATING THROMBOSIS

(71) Applicant: ANDONG NATIONAL UNIVERSITY INDUSTRY-ACADEMIC COOPERATION FOUNDATION, Gyeongsangbuk-do (KR)

(72) Inventor: Ho Yong Sohn, Daegu (KR)

(73) Assignee: ANDONG NATIONAL UNIVERSITY INDUSTRY-ACADEMIC COOPERATION FOUNDATION, Gyeongsangbuk-do (KR)

( * ) Notice: Subject to any disclaimer, the term of this patent is extended or adjusted under 35 U.S.C. 154(b) by 26 days.

(21) Appl. No.: 17/347,338

(22) Filed: Jun. 14, 2021

(65) Prior Publication Data

US 2022/0080009 A1    Mar. 17, 2022

(30) Foreign Application Priority Data

Sep. 15, 2020  (KR) .................. 10-2020-0118136
Dec. 11, 2020  (KR) .................. 10-2020-0172882
Dec. 11, 2020  (KR) .................. 10-2020-0172895

(51) Int. Cl.
*A61K 36/185* (2006.01)
*A61P 7/02* (2006.01)
*A61K 31/015* (2006.01)

(52) U.S. Cl.
CPC .......... *A61K 36/185* (2013.01); *A61K 31/015* (2013.01); *A61P 7/02* (2018.01)

(58) Field of Classification Search
None
See application file for complete search history.

(56) References Cited

FOREIGN PATENT DOCUMENTS

| CN | 105998194 A | 10/2016 |
|---|---|---|
| KR | 1020080059092 A | 6/2008 |
| KR | 1020170080608 A | 7/2017 |

OTHER PUBLICATIONS

Request for the Submission of an Opinion, App. No. KR10-2020-0118136, Filed Sep. 15, 2020, Submitted Nov. 18, 2022, 8 pages.
Request for the Submission of an Opinion, App. No. KR10-2020-0172882, Filed Dec. 11, 2020, Submitted Nov. 18, 2022, 10 pages.
Levendal, et al, "In Vivo Effects of *Cannabis sativa* L. Extract on Blood Coagulation, Fat and Glucose Metabolism in Normal and Streptozocin-Induced Diabetic Rats," African Journal of Traditional Complementary and Alternative Medicines, 2006, 3(4): pp. 1-12.
Srivastava, et al, "Isolation and Characterization of Some Phytochemicals from Indian Traditional Plants," Biotechnology Research International, vol. 2012, Article ID 549850, doi:10.1155/2012/549850, 9 pages.
Formukong, et al, "Cannabinoids, the Active Constituents of *Cannabis sativa* L. Inhibit Both Human and Rabbit Platelet Aggregation," British Journal of Pharmacology, 1987, 92; 601, 1 page.
Notification of Reason for Refusal, App. No. KR10-2020-0118136, dated May 25, 2022, 8 Pages.
Coetzee, et al, "Anticoagulant effects of a Cannabis extract in an obese rat model," Science Direct, Elsevier, www.elsevier.de/phymed, Phytomedicine 14 (2007) 333-337, dx.doi.org/10.1016/j.phymed.2006.02.004, 6 Pages.
Bruci, et al, "First systematic evaluation of the potency of Cannabis sativa plants grown in Albania," Elsevier, journalhomepage:www.elsevier.com/locate/forsciint, http://dx.doi.org/10.1016/j.forsciint.2012.04.032, Forensic Science International 222 (2012) 40-46, 8 Pages.
Komakech, et al, "The Wound Healing Potential of Aspilia africana (Pers.) C.D. Adams (Asteraceae)," Evidence-Based Complementary and Alternative Medicine, Published Jan. 21, 2019, 12 Pages.
De Angelis, et al, "Endocannabinoids Control Platelet Activation and Limit Aggregate Formation under Flow," PLOS ONE, www.plos.one.org, Sep. 2014, vol. 9, Issue 9, e108282, 12 Pages.
Coetzee, et al, "Anticoagulant effects of a Cannabis extract in an obese rat model," 0944-7113/$—see front matter, Copyright 2006 Elsevier GmbH, doi:10.1016/j.phymed.2006.02.004, 5 Pages.
Written Decision on Registration, App. No. KR1020200172895, dated Jan. 6, 2023, 5 Pages.
Batubara,, et al., "Effect of Sniffing of Kencur (*Kaemferia galangal*) Essential Oils in Rats," Proc. IS on Medicinal and Aromatic Plants Eds.: N. Chomchalow et al. Acta Hort. 1023, ISHS 2014, 6 Pages.

*Primary Examiner* — Michael V Meller
(74) *Attorney, Agent, or Firm* — Berkeley Law & Technology Group, LLP

(57) ABSTRACT

Disclosed is a method for preventing or treating thrombosis, the method comprising administering a composition containing a hemp (*Cannabis sativa* L.) leaf or flower extract as an active ingredient. The hemp (*Cannabis sativa* L.) leaf or flower extract inhibits thrombus formation-related enzymes and coagulation factors and exhibits potent antithrombotic activity through inhibitory activity against platelet aggregation which triggers blood clotting, but with no lytic activity on human erythrocytes. In addition to being stable to heat, the extract does not lose the inhibitory activity against coagulation factors and thrombus formation-related enzymes even in the acidic condition of pH 2 and the plasma environment. Therefore, the extract is expected to find applications in preventing and treating thrombosis such as ischemic stroke and hemorrhagic stroke through blood circulation improvement.

2 Claims, 10 Drawing Sheets

METHOD FOR PREVENTING OR TREATING THROMBOSIS

BACKGROUND OF THE INVENTION

1. Field of the Invention

The present disclosure pertains to a method for preventing or treating thrombosis, the method comprising administering a composition comprising a hemp (*Cannabis sativa* L.) leaf or flower extract as an active ingredient.

2. Description of the Prior Art

As a constituent of the human body, blood performs a variety of important functions including delivery of oxygen and nutrients, transport of metabolic waste products and buffering action, body temperature maintenance, osmotic pressure regulation, ion equilibrium maintenance, moisture retention, control of fluid characteristics, maintenance and regulation of blood pressure, and biological defense. Normal blood circulation smoothly proceeds with the complementary control of the coagulation system and the thrombolysis system. The coagulation system is known to involve the mechanism in which platelets adhere to the blood vessel wall and aggregate to form a platelet plug, followed by activating the coagulation cascade system to deposit fibrin on the activated platelets to foil a fibrin thrombus.

The formation of fibrin thrombi is dependent on the activation of thrombin. After being produced and activated through various cascade reactions of many coagulation factors, thrombin converts fibrinogen to fibrin monomers which are polymerized in the presence of calcium. The fibrin polymer binds to platelets and endothelial cells and is crosslinked by factor XIII to form a permanent plug. In addition, thrombin activates platelets, factor V, and factor VII to promote the coagulation cascade, playing a central role in plug formation. Therefore, a thrombin activity inhibitor may be used as a prophylactic and therapeutic agent for various thrombotic diseases resulting from excessive blood coagulation. In the intrinsic thrombus formation pathway, it is known that factor XII, factor XI, factor IX, and factor X are activated in a cascade manner, followed by activation of prothrombin to thrombin. Accordingly, specific inhibition of the coagulation factors is also an important target for developing a therapeutic for thrombotic diseases. Thus far, various anti-coagulant agents, anti-platelet agents, and thrombolytics including heparin, coumarin, aspirin, urokinase, etc., have been used for preventing and treating thrombotic diseases. However, their use is limited due to hemorrhagic side effects, gastrointestinal injury, and hypersensitivity induction, as well as high prices.

Hemp (*Cannabis sativa* L.), which is an annual plant belonging to the family Cannabaceae, has been utilized for producing clothes, shoes, and crafts from hemp fabrics made of the stem peels; paper and construction materials from the stem core; and foods and medicines from the seeds. In addition, hemp seed oil is a valuable plant resource used as oil and cosmetics. However, seed shells, buds, and flowers of hemp are misused as hallucinogens because they include the hallucinogenic component tetrahydrocannabinol (THC).

Hemp may have originated from Central Asia and is now cultivated in various regions across the world. In herbal medicine, hemp has been applied to the treatment of various diseases: hemp roots are used for liberating extravasated blood, treating dystocia, and releasing calculi; hemp stem peels for treating bruises, dysuria, and abdominal distension; *cannabis* from hemp flowers as an anti-asthmatic drug, an analgesic, an anesthetic, and a diuretic; hemp flowers for treating paralysis and itching; and flower buds (powder) for treating dystocia, constipation, gout, and insomnia. Hemp seeds has been applied to the treatment of intractable constipation, polydipsia, various pain diseases, menstrual irregularity, dermal disease, and dysentery and reported to have antineurotic and neuroprotective activities.

In Korea, a strict limitation is imparted to research on hemp leaves the use of which is regulated by a law because it may be misused as a hallucinogen. By contrast, various medical products have been developed in foreign countries using hemp leaves. For example, various cannabinoids were isolated (Bakro F. et al., 2020. J Sep Sci. doi: 10.1002/jssc.201900822; Nagy D U et al., 2019. Chem Biodivers. 16: e1800562) and research into the use of hemp for treatment of insomnia and epilepsy has been performed (Choi S. et al., 2020. J Clin Neurophysiol. 37: 39-49). Other biological activities known for hemp include an insecticidal effect (Ahmed M. et al, 2020, Sci Rep. 10: 522), recovery from peripheral nerve injury (Aziz N. et al., 2019. Pak J Pharm Sci. 32 (Supplementary): 785-792), reduction of blood cholesterol levels (Guo T. et al., 2018. Food Funct. 9: 6608-6617), inhibitory activity against the antibiotic-resistant bacterium MRSA (Chakraborty S. et al., 2018. J Integr Med. 16: 350-357), necrosis inducing activity (Shoyama Y et al., 2008, Plant Signal Behav. 3: 1111-1112), and inhibitory activity against cancer cell growth (Suzuki M. et al., 2017. Nat Prod Commun. 12: 759-761).

The electron microscopic examination on bracteole tissues of hemp flowers (Shin, Min-Chol et al., Korean J. Electron Microscopy 24: 1-12) is the sole research that has been conducted into hemp flowers in Korea, thus far, due to the legal regulation that the use of hemp flowers is prohibited. Relatively active research on hemp flowers has been conducted in foreign countries, reporting that it can be applied to the alleviation and treatment of various diseases including anorexia nervosa, nausea, neuropathic pain, glaucoma, depression, neuralgia, multiple sclerosis, Alzheimer's disease, HIV/AIDS, and cancer (Elsohly, M. A et al., 2017, Prog Chem Org Nat Prod. 103: 1-36; Grof C P L. 2018. Br J Clin Pharmacol. 84: 2463-2467; Grotenhermen F, Muller-Vahl K. 2012, Dtsch Arztebl Int. 109: 495-501).

SUMMARY OF THE INVENTION

A purpose of the present disclosure is to provide a method for preventing or treating thrombosis through inhibition of blood coagulation and platelet aggregation, the method comprising administering a composition containing a hemp (*Cannabis sativa* L.) leaf or flower extract as an active ingredient.

In order to achieve the purpose, the present disclosure comprises administering a composition containing a hemp (*Cannabis sativa* L.) leaf or flower extract as an active ingredient.

BRIEF DESCRIPTION OF THE DRAWINGS

The above and other aspects, features and advantages of the present disclosure will be more apparent from the following detailed description taken in conjunction with the accompanying drawings, in which:

FIG. 1A: solvent control (DMSO), FIG. 1B: aspirin (0.25 mg/ml), FIG. 1C: aspirin (0.12 mg/ml), FIG. 1D: ethanol extract from immature hemp leaf (0.25 mg/ml), FIG. 1E: ethanol extract from mature hemp stem (0.25 mg/ml), FIG. 1F: ethanol extract from mature hemp root (0.25 mg/ml), FIG. 1G: ethanol extract from hemp seed (0.25 mg/ml);

DETAILED DESCRIPTION OF THE EXEMPLARY EMBODIMENTS

Figure 1A:
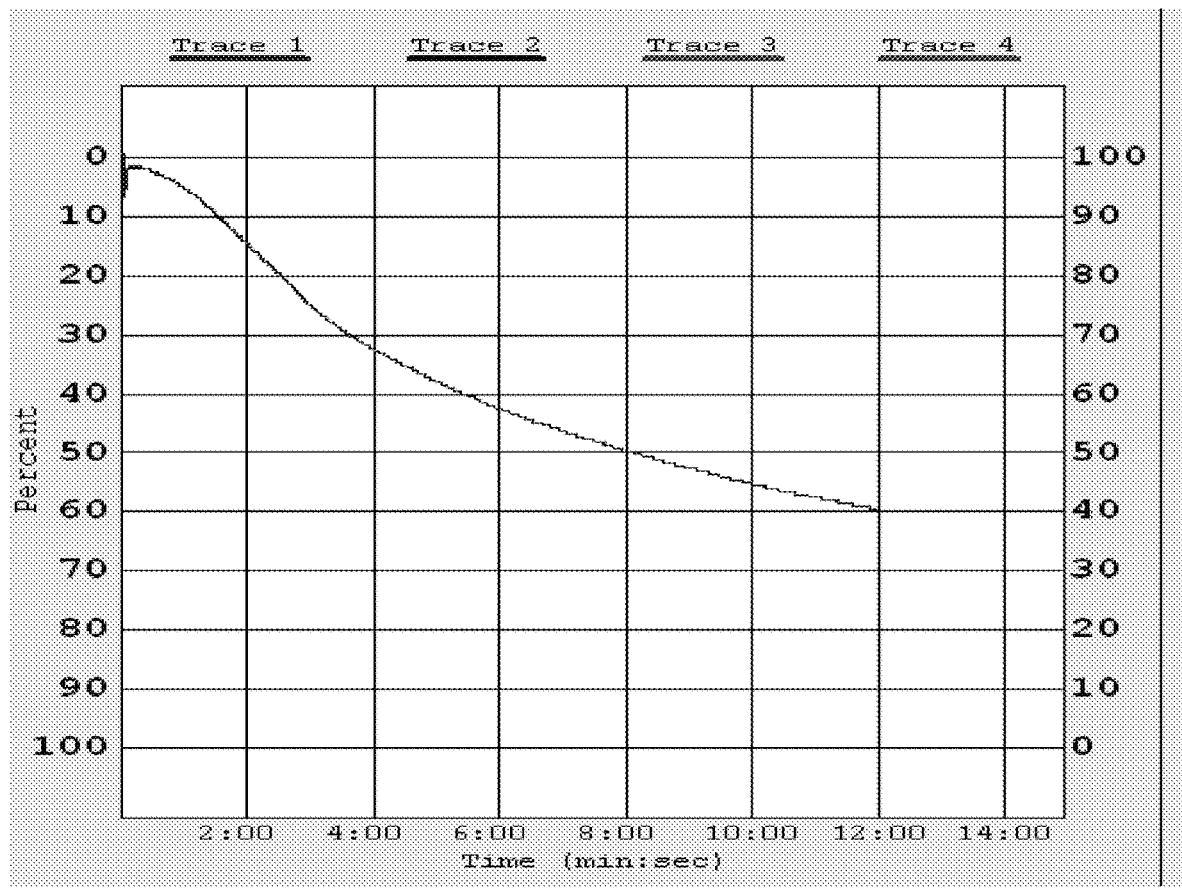
FIG. 1A to 1G shows human platelet aggregation inhibition activity of extracts from hemp parts.
Figure 1B:
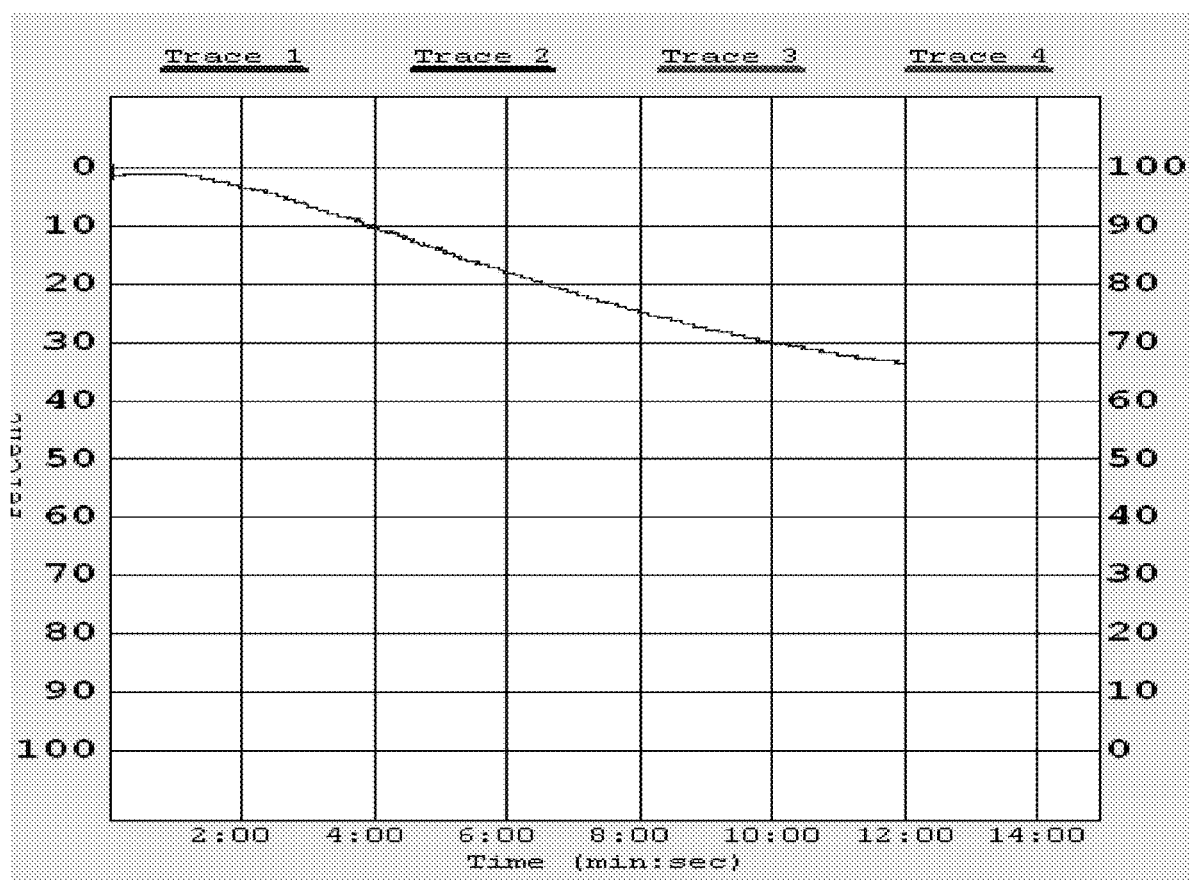
Figure 1C:
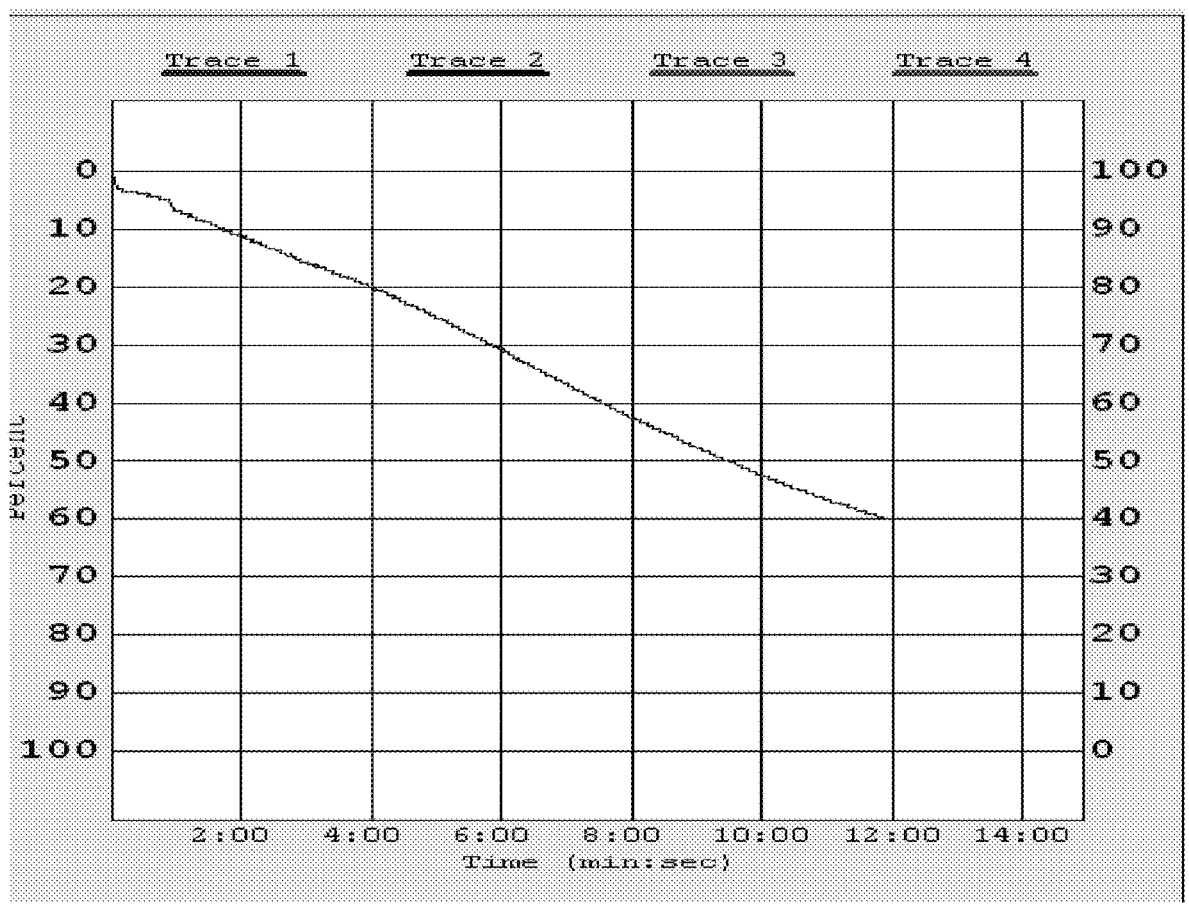
Figure 1D:
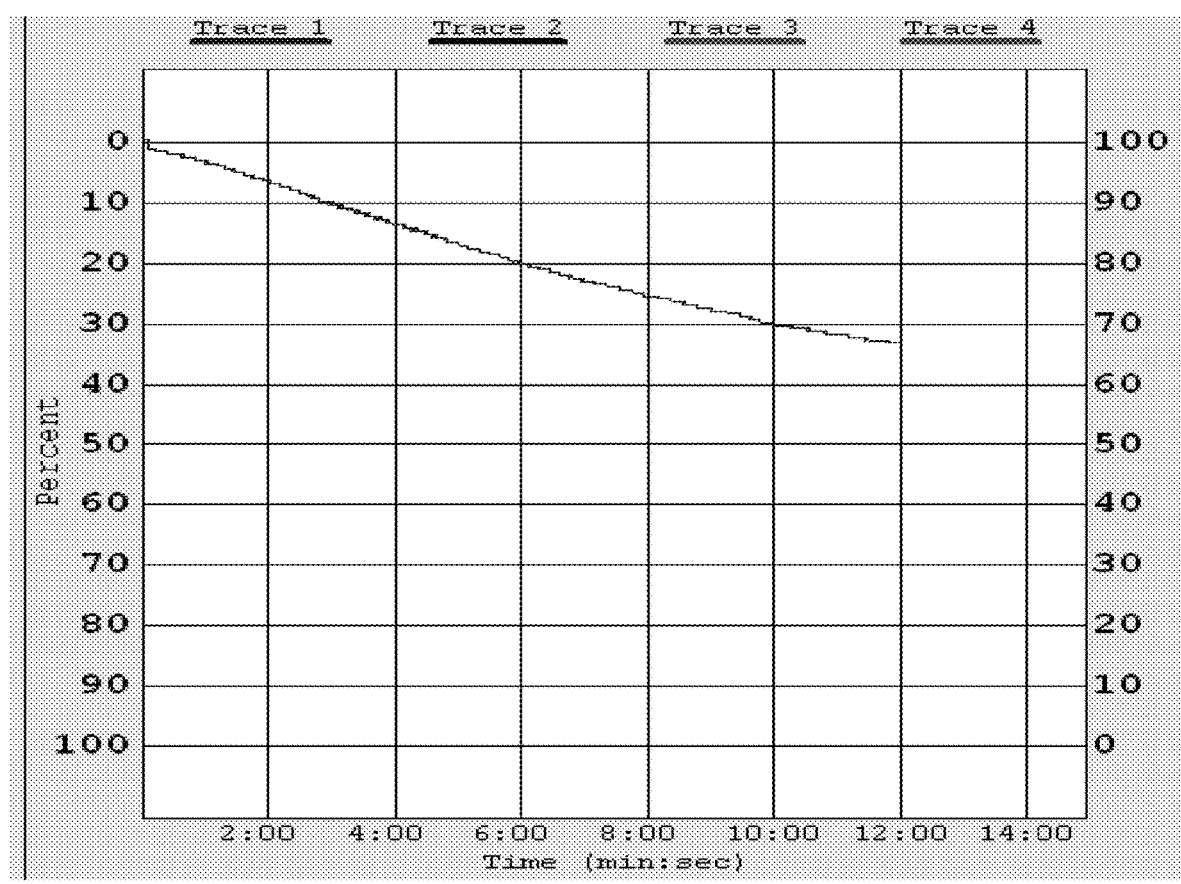
Figure 1E:
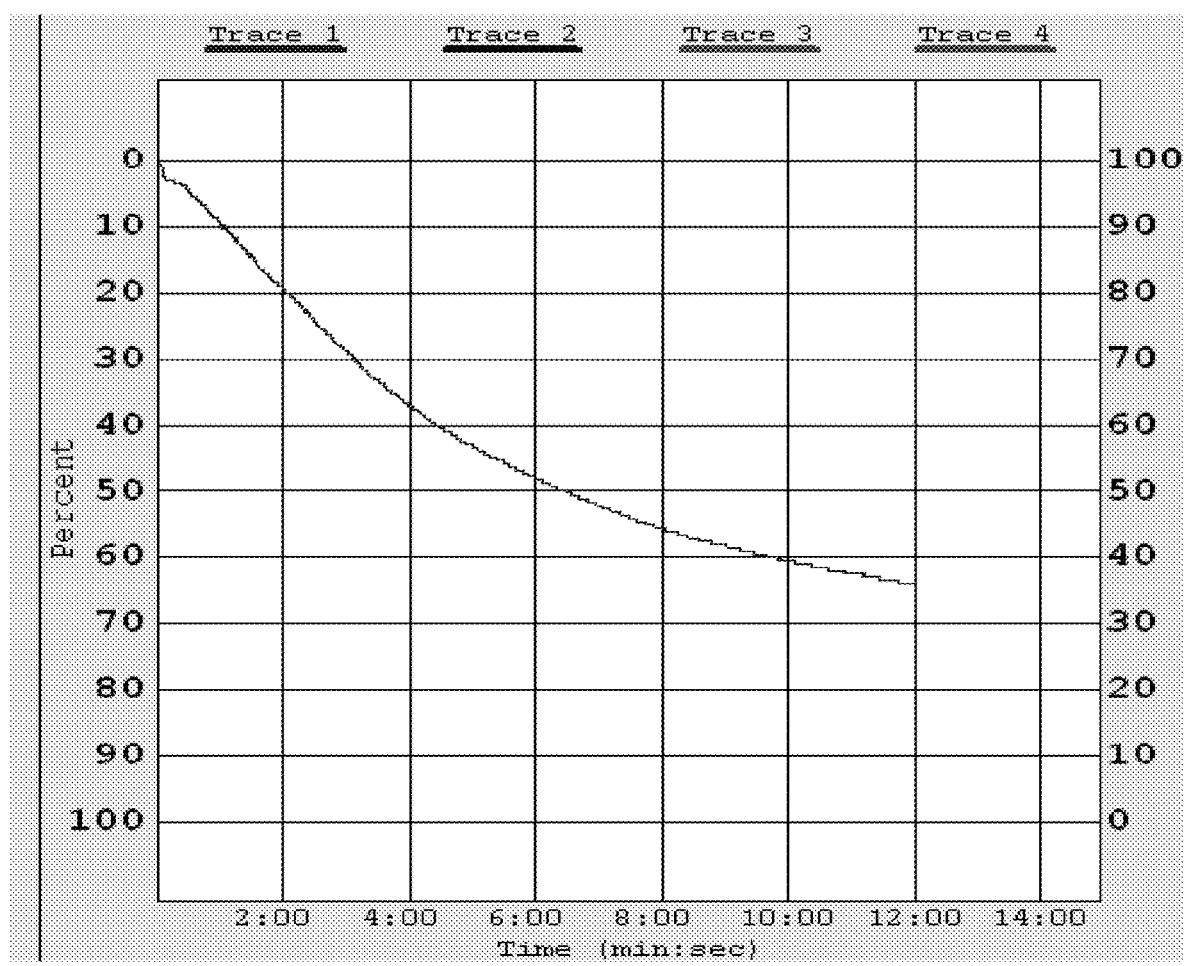
Figure 1F:
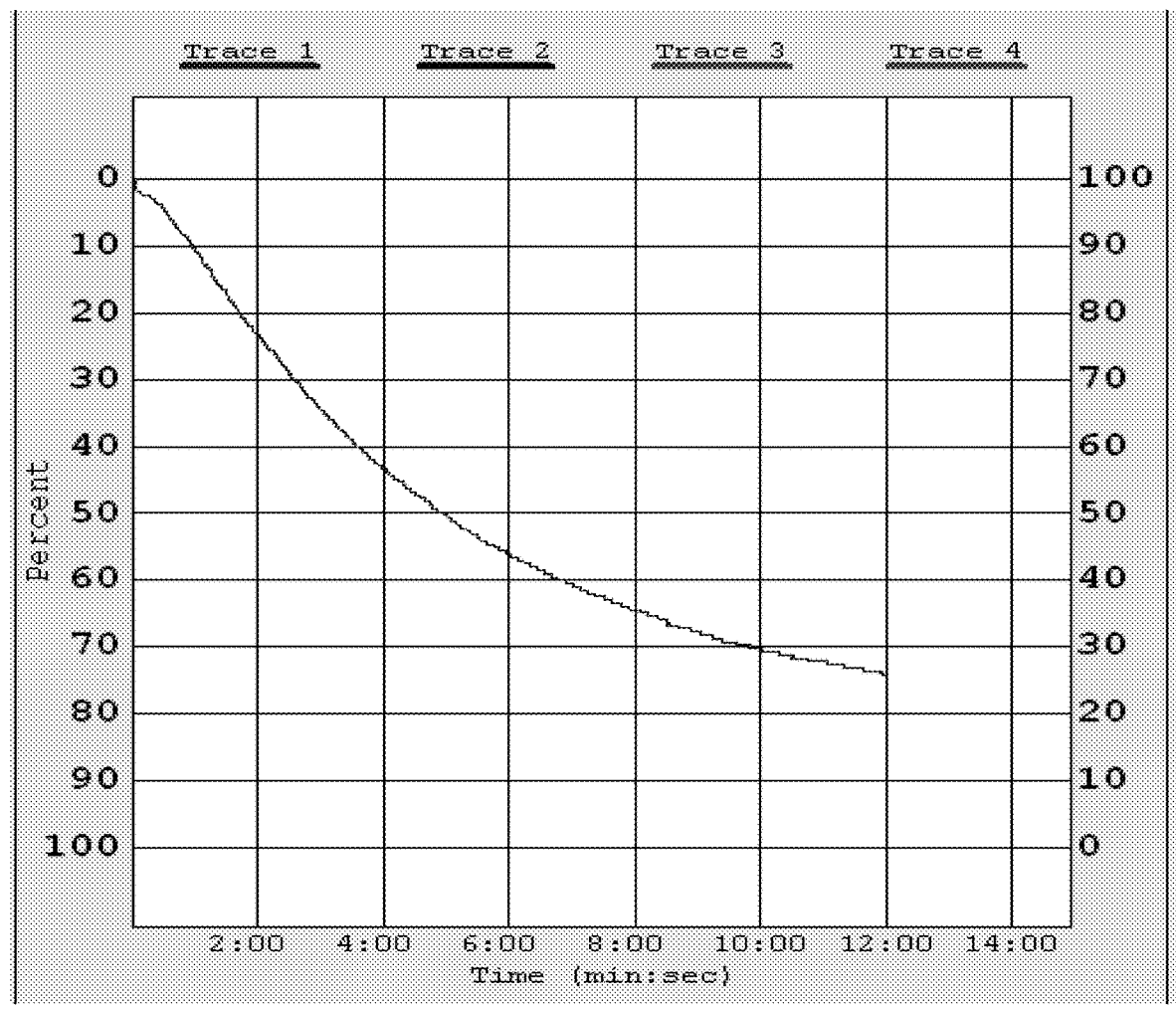
Figure 1G:
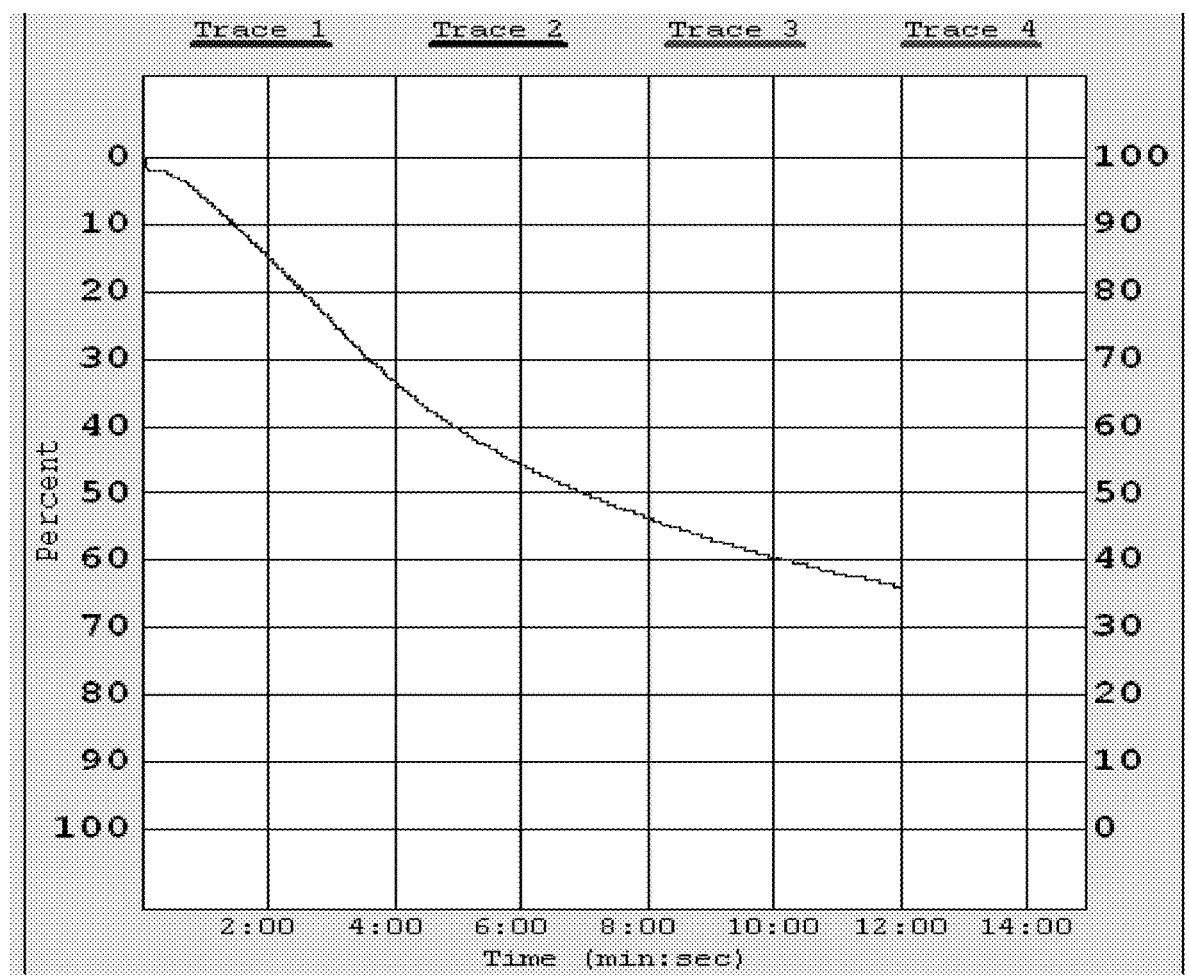

Below, a detailed description will be given of the present disclosure.

<Hemp Leaf Extract>

For use in evaluating anti-thrombotic activity of hemp, extracts from leaves, stems, roots, and seeds of hemp harvested according to maturity periods were prepared. The extracts were assayed for anticoagulant activity and platelet aggregation inhibition activity. As a result, an extract from immature hemp leaves was recovered as an antithrombotic active substance. The extract was further identified to be highly stable to heat and acid without causing the lysis of erythrocytes. Thus, the extract was intended to be used in a method, pharmaceutical composition, and a health functional food for prevention or treatment/alleviation of thrombosis.

In brief, in order to develop a method, a pharmaceutical composition, and a health functional food for prevention or treatment/alleviation of thrombosis by using hemp, which is known in folk medicine to have advantageous effects on various diseases of blood vessels, the circulation system, the digestive system, and the metabolic system, various solvent extracts from leaves, stems, roots, and seeds of hemp harvested according to maturity periods were prepared and assayed for antithrombotic activity in terms of direct thrombin inhibition against human thrombin (thrombin time), prothrombin inhibition (prothrombin time), and activated partial thromboplastin time (aPTT). From the assay, it was found that an extract from leaves of immature hemp (leaf of *Cannabis sativa* L.) has excellent anticoagulant activity and potent platelet aggregation inhibition activity. In addition, the extract was identified to have no lytic activity on human erythrocytes, which allows the practical availability of the extract.

Therefore, the present disclosure provides a method for preventing or treating thrombosis, the method comprising administering a composition containing an immature hemp (*Cannabis sativa* L.) leaf extract as an active ingredient.

The leaf is preferably not thermally treated.

The extract is preferably an ethanol extract.

In addition, the present disclosure provides a composition and a health functional food comprising an immature hemp (*Cannabis sativa* L.) leaf extract for prevention or alleviation of thrombosis.

The leaf is preferably not thermally treated.

The extract is preferably an ethanol extract.

Hereinafter, the preparation method and efficacy assay of an immature hemp (*Cannabis sativa* L.) leaf extract according to the present disclosure will be explained in detail.

The method for preparation and efficacy assay of an immature hemp (*Cannabis sativa* L.) leaf extract according to the present disclosure comprises the steps of: preparing extracts from various parts of hemp harvested according to maturity periods through solvent extraction; evaluating the extracts for antithrombotic activity; and examining stability of an immature hemp leaf extract.

The "immature hemp leaf extract" contained in the composition of the present disclosure may be obtained through the steps of preparing an extract from immature hemp leaves with an organic solvent, and filtering the extract solution through a filter with a pore size of 0.06 mm or less, followed by vacuum concentration. As used herein, the term "immature" is understood as pertaining to the growth of the aerial part of hemp to a height of 1 m or less.

The organic solvent used in the present disclosure may be water (cold or hot), hexane, methylene chloride, acetone, a liquor essence, an anhydrous or hydrated lower alcohol of 1-4 carbon atoms (methanol, ethanol, liquor essences, propanol, butanol, and so on), or a mixed solvent of the lower alcohol and water, with preference for hot water or 95% ethanol extraction.

In particular embodiments of the present disclosure, the immature hemp leaf extract may be an ethanol extract from leaves of young hemp with the aerial part 1 m or less tall. In addition, the leaves are preferably not subject to separate thermal treatment. Here, the ethanol extract may be fractioned with the organic solvents of hexane, ethyl acetate, and butanol, sequentially or separately, to obtain a hexane fraction, an ethyl acetate fraction, a butanol fraction, and a water residue additionally.

In the present disclosure, ethanol extracts were prepared from various parts of hemp harvested according to maturity periods, each adjusted into a concentration of 5 mg/ml, and measured for thrombin time, prothrombin time, and aPTT. From the measurements, it was found that extracts from immature leaves, matured stems, and matured roots inhibit thrombus formation because it exhibited more potent inhibitory activity against coagulation factors than 1.5 mg/ml aspirin does. Moreover, the extracts from immature leaves, matured stems, and matured roots also inhibited prothrombin to the extent as high as those made by 1.5 mg/ml aspirin. By contrast, a hemp seed extract exhibited a negligible anticoagulant activity, compared to aspirin (1.5 mg/ml).

Ethanol extracts from various parts of hemp harvested according to maturity periods were each adjusted into a concentration of 0.25 mg/ml and assayed for platelet aggregation inhibition activity. As a result, the hemp seed extract exhibited almost no anti-aggregation effects as its inhibition was almost the same as that of a non-added control. Moreover, extracts from matured stem and matured roots allowed platelet aggregation by 124% and 148%, respectively, compared to the non-added control, thus exhibiting thrombus formation promoting activity. In contrast, the immature hemp leaf extract allowed platelet aggregation 56% lower than the non-added control, showing potent platelet aggregation inhibition activity, which is as high as that made by aspirin having the same concentration. These data implicate that extracts from various parts of hemp have a broad spectrum of activities with respect to thrombus formation and particularly, the immature hemp leaf extract possesses antithrombotic activity by potently inhibiting platelet aggregation as well as coagulation factors and can serve as an alternative to conventional antiplatelet agent with high side effects, such as aspirin.

The immature hemp leaf extract of the present disclosure may be prepared into powder through a typical powdering process such as vacuum drying and lyophilization or spray drying. The extract is not degraded by various enzymes in plasma and maintains activity even under the thermal treatment of 100° C. as well as at a pH of 2 in the human gastric environment.

The active ingredient of the present disclosure may be used for preventing or treating various thrombosis-related diseases. Examples of the diseases include arterial thrombosis, such as acute myocardial infarction, chest pain, dyspnea, loss of consciousness, ischemic stroke, hemorrhagic stroke, headache, motor abnormality, dysaesthesia, change of character, decreased vision, epileptic seizure, pulmonary thrombosis, deep vein thrombosis, lower limb edema, pain, and acute peripheral arterial obstruction, and venous thrombosis, such as deep vein thrombosis, portal vein thrombosis, acute renal vein obstruction, cerebral venous thrombosis, and subclavian vein obstruction.

The pharmaceutical composition comprising the active ingredient of the present disclosure can be used in the various forms such as oral dosage forms of powders, granules, tablets, capsules, suspensions, emulsions, syrups, aerosols, and injections of a sterile injectable solution formulated by the conventional method to serve the purpose of each form, and can be administered through various routes including oral administration or intravenous, intraperitoneal, subcutaneous, rectal, and topical administration.

The pharmaceutical composition may further comprise a carrier, an excipient, or a diluent. Examples of available suitable carriers, excipients, or diluents include lactose, dextrose, sucrose, sorbitol, mannitol, xylitol, erythritol, maltitol, starch, acacia rubber, alginate, gelatin, calcium phosphate, calcium silicate, cellulose, methyl cellulose, amorphous cellulose, polyvinyl pyrrolidone, water, methyl hydroxy benzoate, propyl hydroxy benzoate, talc, magnesium stearate, and mineral oil. The pharmaceutical compositions of the present disclosure may further comprise fillers, anti-coagulants, lubricants, humectants, fragrances, emulsifiers, preservatives, etc.

In a particular embodiment, solid formulation agents for oral administration include tablets, pills, powders, granules, and capsules, and such solid dosage forms are formulated by mixing the pharmaceutical composition in the present disclosure with one or more excipients, such as starch, calcium carbonate, sucrose, lactose, gelatin, and so on. Also, lubricants such as magnesium stearate and talc can be used in addition to simple diluents.

In a particular embodiment, liquid formulations for oral administration can be exemplified by suspensions, solutions, emulsions, and syrups, and may include various excipients such as humectants, sweeteners, fragrances, and preservatives, in addition to liquid paraffin and water which are commonly used as simple diluents.

In a particular embodiment, formulations for parenteral administration may be exemplified by sterile aqueous solutions, nonaqueous solvents, suspending agents, emulsions, lyophilization agents, and suppository agents. Nonaqueous solvents and suspending agents may include propylene glycol, polyethylene glycol, vegetable oil such as olive oil, and injectable esters such as ethyl oleate. Injections may include conventional additives such as solvents, isotonic agent, suspending agents, emulsifiers, stabilizers, and preservatives.

The active ingredient of the present disclosure is administrated in a pharmaceutically effective amount. As used herein, the term "pharmaceutically effective amount" refers to the amount which is applicable to the medical treatment and sufficient to treat the diseases with a reasonable benefit/risk ratio, and the level of effective amount can be determined depending on type and severity of patient's disease, activity of the drug, sensitivity on the drug, time of administration, route of administration, discharge rate, duration of treatment, factor including other medications that are used simultaneously, and other factors well-known in the field of medicine. The composition of the present disclosure may be administered as individual therapy or in combination with other therapies, simultaneously with or sequentially to conventional therapies and once or multiple times. It is important to administer the minimum amount which can provide the maximum effect without the side effects in consideration of all the above factors, which can be easily determined by those skilled in the art.

In a particular embodiment, an effective amount of the active ingredient in the pharmaceutical composition of the present disclosure may vary depending on age, sex, and body weight of the patient, and 1 to 5,000 mg in general, or 100 to 3,000 mg preferably per kg of the body weight can be administered every day, every other day, or one to three times a day. However, the dosage may be increased or decreased depending on the route of administration, the severity of the disease, sex, body weight, age, etc., and therefore does not in any way limit the scope of the present disclosure.

The pharmaceutical composition of the present disclosure may be administered to subjects via various routes. All modes of administration can be contemplated, for example, including oral administration, or intrarectal, intravenous, intramuscular, subcutaneous, and endometrial or intracerebroventricular injections.

As used herein, the term "administration" refers to provision of a prescribed substance to the patient in an appropriate manner, and the pharmaceutical composition of the present disclosure can be administrated orally or parenterally through all the general routes as long as it can reach the target tissue. Also, the composition in the present disclosure can be administered by any device that is able to deliver the active ingredient of the pharmaceutical composition to target cells.

As used herein, the term "subject" refers to the animal comprising, but not limited to, a human, a monkey, cattle, a horse, sheep, a pig, a chicken, a turkey, a quail, a cat, a dog, a mouse, a rat, a rabbit, or a guinea pig, with preference for mammals and greater preference for humans.

In addition, the health functional food of the present disclosure can be used in various food forms and beverages for preventing or alleviating thrombosis. Examples of the foods containing the active ingredient of the present disclosure include various kinds of foods, beverages, chewing gums, teas, vitamin complex, health supplementary foods, etc., and can be used in the form of powders, granules, tablets, capsules, or drinks.

The active ingredient of the present disclosure may be in an amount of 0.01 to 15% by weight, based on the total weight of the food and may be added at a ratio of 0.02 to 10 g, preferably at a ratio of 0.3 to 1 g per 100 ml of a health beverage.

Health functional foods of the present disclosure may contain not only the above compounds as essential ingredients in the indicated proportion, but also sitologically acceptable food supplementary additives, such as various flavoring agents and natural carbohydrates as additional ingredients.

Examples of the aforementioned natural carbohydrate include typical sugars, e.g., monosaccharides such as glucose, fructose, and so on, disaccharides such as maltose, sucrose, and so on, and polysaccharides such as dextrin, cyclodextrin, and so on, and sugar alcohol such as xylitol, sorbitol, erythritol, and so on.

The flavoring agent may be a natural flavoring agent, such as thaumatin, *stevia*, e.g., rebaudioside A or glycyrrhizin, or a synthetic flavoring agent such as saccharin, aspartame, etc. The proportion of the above natural carbohydrate is typically about 1 to 20 g, or preferably about 5 to 12 g per 100 ml of health functional food in the present disclosure. In addition to the foregoing additives, the health functional food of the present disclosure may contain various nutritional supplements, vitamins, minerals, flavoring agents such as natural flavoring agents and synthetic flavoring agents, colorants and weighting agents, pectic acid and salts thereof, alginic acid and salts thereof, organic acid, protective colloid thickeners, pH control agents, stabilizers, preservatives, glycerin, alcohol, carbonization agent used in carbonated beverage. In addition, the health functional food of the present disclosure may include pulp for preparing natural fruit juices, fruit juice beverage, and vegetable beverage. These components can be used independently or in combination. The proportion of these additives is selected typically in the range of 0.01 to 20 parts by weight per 100 parts by weight of the active ingredient of the present disclosure.

Hereinafter, the present disclosure will be described in more detail with reference to Examples. The following Examples are only preferred embodiments of the present disclosure, and the scope of the present disclosure is not limited by the following Examples.

EXAMPLES

All experiments, including hemp cultivation, harvesting, extraction, and activity evaluation, were conducted legally in accordance with the approval for narcotic drug use, the license to handle narcotic drug raw materials, and the permit to culture *cannabis*.

Example 1: Preparation of Ethanol Extracts from Various Parts of Hemp According to Maturity Periods and Analysis of Valuable Ingredient Thereof A harvest was made of leaves of immature young hemp with the aerial part 1 m or less tall on June 2018 and stems and roots of matured hemp on July 2018. Seeds of hemps harvested in 2018 were purchased from a domestic market. Ethanol extracts were prepared from the plant materials. In brief, each material was added with 10 volumes of an organic solvent, followed by two rounds of extraction at room temperature. The extract solutions thus formed were pooled, filtered, and concentrated at a reduced pressure to afford an ethanol extract as a powder. Extraction yields from various parts of hemp and analysis results of the valuable ingredients thereof are summarized in Table 1, below.

TABLE 1

Extraction Yield from Various Parts of Hemp and Analysis of Valuable Ingredients thereof

| Extract | Extraction Yield (%) | Contents (mg/g) | | | |
| --- | --- | --- | --- | --- | --- |
| | | Total Polyphenol | Total flavonoid | Total sugar | Reducing sugar |
| Leaf | 6.0 | 43.2 ± 2.0 | 29.1 ± 1.1 | 117.5 ± 0.7 | 74.9 ± 7.3 |
| Stem | 9.4 | 3.0 ± 0.3 | 3.8 ± 1.7 | 120.0 ± 5.8 | 49.9 ± 6.7 |
| Root | 1.4 | 13.4 ± 0.8 | 2.7 ± 0.3 | 153.5 ± 8.2 | 41.1 ± 10.1 |
| Hemp seed | 9.8 | 0.8 ± 0.4 | 2.1 ± 0.7 | 12.0 ± 0.5 | 12.6 ± 1.0 |

As high as 9.4-9.8% was measured for the yield of extraction from hemp seeds and stems. The extraction yield for hemp leaves was also as high as 6%. By contrast, an extraction yield of as low as 1.4% was obtained for hemp roots. For valuable ingredient analysis, the extracts were measured for total polyphenols, total flavonoids, total sugars, and reducing sugars. A content of total polyphenols was determined by mixing 400 µl of a test liquid with 50 µl of Folin-Ciocalteau and 100 µl of $Na_2CO_3$ saturated solution, leaving the mixture at room temperature for 1 hour, and reading absorbance at 725 nm, with tannic acid serving as a standard reagent. For a content of total flavonoids, an extract was prepared by stirring each sample in methanol for 18 hours and 400 µl of a filtrate from the extract was added with 4 ml of 90% diethylene glycol and then with 40 µl of 1 N NaOH and reacted at 37° C. for 1 hour, followed by reading absorbance at 420 nm. Rutin was used as a standard reagent. Reducing sugars and total sugars were quantitated using DNS and phenol-sulfuric acid methods, respectively.

As shown in Table 1, the polyphenol content peaked at 43.2 mg/g from the leaf extract while being measured to be as very low as 0.8 mg/g in the seed extract. The leaf extract was also measured to have the highest total flavonoid content of 29.1 mg/g while relatively low total flavonoid contents of 2.1-2.7 mg/g was measured in the extracts from roots and seeds. Thus, the leaf extract was found to have higher contents of polyphenols and flavonoids than stem, root, and seed extracts. Total sugar contents were in the order of root extract (153.5 mg/g)>stem extract (120.0 mg/g), leaf extract (117.5 mg/g)>seed extract (12.0 mg/g) while total reducing sugar contents were in the order of leaf extract (74.9 mg/g)>stem extract (49.9 mg/g), root extract (41.1 mg/g)>seed extract (12.6 mg/g). That is, the hemp leaf extract was identified to contain significant amounts of total sugars and reducing sugars.

Example 2: Evaluation for Anticoagulant Activity of Extracts from Various Parts of Hemp Harvested According to Maturity Period Extracts from various parts of hemp in Example 1 were assayed for inhibitory activity against blood coagulation, and the results are summarized in Table 2. In this regard, the assay for anticoagulant activity of hemp extracts was conducted according to the methods reported previously (Sohn et al., 2004. Kor. J. Pharmacogn 35. 52-61; Kwon et al., 2004. J. Life Science, 14. 509-513; and Ryu, et al., 2010. J. Life Science, 20. 922-928) to evaluate thrombin time, prothrombin time, and aPTT. In this assay, commercially available control plasma (MD Pacific Technology Co., Ltd, Huayuan Industrial Area, China) was used, and tests for thrombin time, prothrombin time, and aPTT were carried out as follows.

Thrombin Time

At 37° C., 10 μl of each of sample extracts having various concentrations was mixed and reacted with 50 μl of 0.5 U thrombin (Sigma Co., USA) and 50 μl of 20 mM $CaCl_2$ for 2 min in an Amelung coagulometer KC-1A tube (Japan). After 100 μl of plasma was added to the mixture, the time it takes for a clot to form in the plasma was measured. As a control, aspirin (Sigma Co., USA) was used while DMSO, instead of the samples, served as a solvent control. For DMSO, the time taken to form a clot was 32.1 seconds. The thrombin time that accounts for a thrombin inhibition effect was expressed as a mean value of measurements from three or more independent experiments. Antithrombotic activity was explained by a ratio of the thrombin time in the presence of a sample to that in the presence of the solvent control.

Prothrombin Time

In an Amelung coagulometer KC-1A tube (Japan), 70 μl of standard plasma (MD Pacific Co., China) was heated, together with 10 μl of each of samples having various concentrations, at 37° C. for 3 min before adding 130 μl of PT reagent thereto. The time taken for a clot to form in the plasma was measured. This experiment was repeated three times independently. The prothrombin time was expressed as a mean value of the three measurements. As a control, aspirin (Sigma Co., USA) was used while DMSO, instead of the samples, served as a solvent control. For DMSO, the time taken to form a clot was 18.1 seconds. Anti-prothrombotic activity was explained by a ratio of the prothrombin time in the presence of a sample to that in the presence of the solvent control.

aPTT (activated Partial Thromboplastin Time)

In an Amelung coagulometer KC-1A tube (Japan), 10 μl of each of sample extracts having various concentrations was heated, together with 100 μl of plasma, at 37° C. for 3 min and added with 50 μl of aPTT reagent (Sigma, ALEXIN™), followed by incubation at 37° C. for 3 min, again. Subsequently, 50 μl of $CaCl_2$ (35 mM) was added. Then, the time it takes for a clot to form in the plasma was measured. Instead of samples, DMSO served as a solvent control. For DMSO, the time taken to form a clot was 55.1 seconds. The aPPT was expressed as a mean value of the measurements of three independent experiments. Blood coagulation factor inhibition activity was explained by a ratio of the aPPT in the presence of a sample to that in the presence of the solvent control.

TABLE 2

Blood Coagulation Inhibition Activity of Extracts from Various Parts of Hemp Harvested According to Maturity Period

| Control/Extract | Conc. (mg/ml) | Blood Coagulation Inhibition Activity* | | |
|---|---|---|---|---|
| | | Thrombin time | Prothrombin time | aPTT |
| Solvent Control (DMSO) | — | 1.00 ± 0.02 | 1.00 ± 0.01 | 1.00 ± 0.00 |
| Aspirin | 1.5 | 1.83 ± 0.03 | 1.29 ± 0.03 | 1.48 ± 0.03 |
| Leaf | 5.0 | 0.95 ± 0.00 | 1.32 ± 0.04 | 1.84 ± 0.22 |
| Stem | 5.0 | 1.04 ± 0.08 | 1.21 ± 0.02 | 1.90 ± 0.42 |
| Root | 5.0 | 1.13 ± 0.02 | 1.28 ± 0.02 | 1.89 ± 0.25 |
| Seed | 5.0 | 1.09 ± 0.01 | 0.86 ± 0.12 | 1.19 ± 0.06 |

*Blood coagulation inhibition activity: time taken for a clot to form in sample added group/time taken for a clot to form in DMSO added group Thrombin time, prothrombin time, and aPTT measurements of extracts prepared from various parts of hemp, each having 5 mg/ml, are given in Table 2. As can be understood from the data, the extracts from leaves, stems, and roots exhibited excellent inhibitory activity against coagulation factors, with 1.84- to 1.90-fold prolonged aPTT than the non-added control. The aPTT was superior to that of aspirin (1.5 mg/ml) used as a control for inhibiting thrombus formation, which was 1.48-fold prolonged. In addition, the extracts from hemp leaves, stems, and roots were observed to have anti-prothrombic activity comparable to that of aspirin. However, poor antithrombic activity was detected from the leaf, stem, and root extracts. As for the seed extract, its anticoagulant activity was slight, with no significant inhibitory effects on blood clotting. Therefore, extracts from hemp leaves, stems, and roots were considered to be able to suppress thrombus formation by inhibiting various coagulation factors and prothrombin.

Example 3: Platelet Aggregation Inhibition Activity of Extracts from Various Part of Hemp Harvested According to Maturity Periods The extracts from various parts of hemp, prepared in Example 1, were evaluated for human platelet aggregation inhibition activity, and the results are given in Table 3 and FIG. 1.

Platelets are cells that have biconvex discoid structures and circulate, together with various hemocytes, through blood vessels. Platelets have no cell nucleus, but cytoplasmic granules containing high concentrations of various substances associated with protection from blood vessel injury and with platelet aggregation. When the endothelial lining is injured, platelets cells secrete coagulation factors and adhere to the collagen exposed from the injured endothelial cells to form primary hemostatic plug. Hence, platelet aggregation inhibition is an important role in preventing blood clotting. Platelet aggregation inhibition activity was evaluated according to the following method.

Platelet Aggregation Inhibition Activity Human enriched platelets were used. They were washed once with a washing buffer (138 mM NaCl, 2.7 mM KCl, 12 mM $NaHCO_3$, 0.36 mM $NaH_2PO_4$, 5.5 mM Glucose, 1 mM EDTA, pH 6.5) and then resuspended in a suspending buffer (138 mM NaCl, 2.7 mM KCl, 12 mM $NaHCO_3$, 0.36 mM $NaH_2PO_4$, 5.5 mM Glucose, 0.49 mM $MgCl_2$, 0.25% gelatin, pH 7.4). Centrifugation at 3,000 rpm for 10 min was followed by resuspension in a suspending buffer, with the platelets adjusted to the density of $4\times10^9$/ml. Subsequently, 1 ml of the suspension was incubated with 2.5 μl of collagen for 5 min, after which platelet aggregation was measured at 37° C. using a whole-blood aggregometer (Chrono-log, USA).

TABLE 3

Platelet Aggregation Inhibition Activity of Extracts from Various Parts of Hemp Harvested According to Maturity Period

| Control/Extract | Conc. (mg/ml) | Platelet Aggregation Curve | | | | |
|---|---|---|---|---|---|---|
| | | Amplitude (ohm) | Slope | Lag time (sec) | Area under curve | Platelet Aggregation Activity(%)* |
| Solvent Control (DMSO) | | 14 | 3 | 36 | 94.9 | 100.0 |
| Aspirin | 0.25 | 8 | 1 | 128 | 47.2 | 49.7 |
| | 0.125 | 14 | 2 | 35 | 78.0 | 82.2 |

TABLE 3-continued

Platelet Aggregation Inhibition Activity of Extracts from Various
Parts of Hemp Harvested According to Maturity Period

| Control/Extract | Conc. (mg/ml) | Platelet Aggregation Curve | | | | Platelet Aggregation Activity(%)* |
|---|---|---|---|---|---|---|
| | | Amplitude (ohm) | Slope | Lag time (sec) | Area under curve | |
| Leaf | 0.25 | 8 | 1 | 40 | 53.1 | 56.0 |
| Stem | 0.25 | 15 | 2 | 20 | 118.4 | 124.8 |
| Root | 0.25 | 18 | 3 | 17 | 140.8 | 148.4 |
| Seed | 0.25 | 14 | 2 | 29 | 100.6 | 106.0 |

*Platelet Aggregation Activity: Area under curve for sample added group/area under curve for DMSO added group] × 100

As shown in Table 3 and FIG. 1, aspirin allowed platelet aggregation by 49.7% at a concentration of 0.25 mg/ml and by 82.2% at a concentration of 0.125 mg/ml. This excellent platelet aggregation inhibition activity proved why aspirin is clinically used as an antithrombotic agent. The hemp seed extract with a concentration of 0.25 mg/ml did not have any influence on platelet aggregation, and the extracts from stems and roots allowed platelet aggregation by 124.8% and 148.4%, respectively, at a concentration of 0.25 mg/ml and thus promoted platelet aggregation. However, the leaf extract with a concentration of 0.25 mg/ml proved potent platelet aggregation inhibition activity by exhibiting 56.0% platelet aggregation compared to the non-added control. The data thus obtained implied that the non-heated ethanol extract from immature hemp leaves regulates thrombus formation-related elements including prothrombin and coagulation factors and has potent inhibitory activity against platelet aggregation, thus finding availability as an antithrombotic agent.

Example 4: Human Erythrocyte Lysis Activity of Ethanol Extract of Immature Hemp Leaf In foreign countries, hemp leaves have been applied to foods and used as a therapeutic assistant for peripheral nerve injury (Aziz N. et al., 2019. Pak J Pharm Sci. 32 (Supplementary): 785-792) and thus are guaranteed safe for use in foods. However, objective evaluation for the safety of extracts from various hemp parts has not been made. Thus, the extracts were evaluated for acute toxicity in teems of human erythrocyte lysis.

In this regard, erythrocyte lysis activity was assayed as reported previously (Sohn, Ho-Yong, 2014. Korean J. Microbiol. Biotechnol. 42: 285-292). Briefly, 100 μl of human erythrocytes, after being washed three times with PBS, was added to each well of 96-well microplates, mixed with 100 μl of each of samples having various concentrations, and incubated at 37° C. for 30 min. Subsequently, the reaction mixture was centrifuged for 10 min (1,500 rpm). After 100 μl of the supernatant was transferred to new microtiter plates, absorbance was read at 414 nm to analyze hemoglobin release according to hemolysis. DMSO (2%) was used as a solvent control for the samples while Triton X-100 (1 mg/ml) served as a control for hemolysis. Hemolysis activity was calculated according to the following equation:

(%)Hemolysis=[(Abs. *S*–Abs. *C*)/(Abs. *T*–Abs. *C*)]×100

Abs. S: Absorbance of sample
Abs. C: Absorbance of DMSO
Abs. T: Absorbance of Triton X-100 added control

TABLE 4

Human Erythrocyte Lysis Activity of Extracts from Various
Parts of Hemp Harvested According to Maturity Period

| Control/Extract | Conc. (mg/ml) | Human Hemolytic Activity (%) |
|---|---|---|
| Distilled water | — | 0.2 ± 0.3 |
| Solvent (DMSO) | — | 1.5 ± 1.2 |
| Triton X-100 | 1.0 | 100.0 ± 0.1 |
| Amphotericin B | 0.1 | 95.8 ± 0.3 |
| | 0.05 | 80.7 ± 7.3 |
| | 0.025 | 59.5 ± 6.3 |
| | 0.0125 | 48.2 ± 5.9 |
| | 0.0063 | 38.0 ± 0.7 |
| | 0.0032 | 26.5 ± 9.6 |
| | 0 | 0.0 ± 1.7 |
| Leaf | 1.0 | −10.9 ± 2.1 |
| Stem | 1.0 | −7.0 ± 0.2 |
| Root | 1.0 | −15.0 ± 1.2 |
| Seed | 10 | 90.8 ± 0.8 |
| | 0.5 | 94.3 ± 0.6 |
| | 0.25 | 72.1 ± 0.1 |
| | 0.125 | 4.0 ± 3.2 |

As shown in Table 4, no hemolysis was detected from the controls DMSO and water while Triton X-100 induced 100% hemolysis at a concentration of 1 mg/ml. In addition, amphotericin B, which is used as an anticancer agent and an antifungal agent, lysed erythrocytes by 50% or more at a concentration of 0.025 mg/ml.

On the other hand, the extracts from hemp leaves, stems, and roots were identified to be free of acute toxicity and hemolytic activity as none of them induced hemolysis at a concentration of up to 1 mg/ml. However, seed extracts exhibited the potent hemolytic activity of 90.8% at a concentration of 1 mg/ml and lysed erythrocytes by 72.1% even at a concentration of 0.25 mg/ml. These data suggest that the ethanol extract of immature hemp leaves according to the present disclosure can be used as an alternative to conventional antithrombotic agents having side effects, such as aspirin, without hemolytic activity.

Example 5: Assay for Plasma, Acid, and Heat Stability of Ethanol Extract of Immature Hemp Leaf The ethanol extract of immature hemp leaves obtained in Example 1 was assayed for plasma, heat, and acid stability for blood clotting inhibition and platelet aggregation inhibition activity. Even after being treated at 100° C. for 1 hour, at pH 2 (0.01M HCl) for 1 hour, or in plasma for 1 hour, the extract did not decrease in blood clotting inhibition and platelet aggregation inhibition activity. Thus, the active ethanol extract of immature hemp leaves was observed to contain an active antithrombotic entity stable to acid and heat and can be highly available in practice.

<Hemp Flower Extract>

For use in evaluating anti-thrombotic activity of hemp, extracts from flowers, leaves, stems, roots, and seeds of hemp harvested according to maturity periods were prepared. The extracts were assayed for anticoagulant activity and platelet aggregation inhibition activity. As a result, an extract from hemp flowers was recovered as an antithrombotic active substance. The extract also exhibited lytic activity on human erythrocytes and thus was divided into an antithrombotic component and a hemolytic component. To this end, the hemp flower extract was fractioned with organic solvents in a sequential manner. The hexane and ethyl acetate fractions thus recovered exhibited more potent antithrombic activity, but was relatively low in hemolytic activity. Particularly, the ethyl acetate fraction was observed to be highly stable to heat and acid, with no contents of THC. Accordingly, the hemp flower extract, and hexane and ethyl acetate fractions thereof were intended to be used in a method, pharmaceutical composition, and a health functional food for prevention or treatment/alleviation of thrombosis.

In brief, in order to develop a pharmaceutical composition, and a health functional food for prevention or treatment/alleviation of thrombosis by using hemp, which is known in folk medicine to have advantageous effects on various diseases of blood vessels, the circulation system, the digestive system, and the metabolic system, various solvent extracts from hemp flowers, leaves, stems, roots, and seeds were prepared and assayed for antithrombotic activity in terms of direct thrombin inhibition against human thrombin (thrombin time), prothrombin inhibition (prothrombin time), and activated partial thromboplastin time (aPTT). From the assay, it was found that an extract from hemp flowers (flowers of Cannabis sativa L.) has the most potent anticoagulant activity. Afterwards, the hemp flower extract was fractioned with organic solvents in a sequential manner. Hexane and ethyl acetate fractions were recovered as they exhibited more potent antithrombic activity than the others. The ethyl acetate fraction was observed to have high stability to heat and acid, without containing THC, and be poor in hemolytic activity, which allows the practical availability of the fraction.

Therefore, the present disclosure provides a method for preventing or treating thrombosis, the method comprising administering a composition containing hemp (Cannabis sativa L.) flower extract as an active ingredient.

The flower is preferably immature inflorescence.

The extract is preferably an ethanol extract.

The extract is preferably a hexane fraction or an ethyl acetate fraction of the ethanol extract.

In addition, the present disclosure provides a composition and a health functional food comprising a hemp (Cannabis sativa L.) flower extract for prevention or alleviation of thrombosis.

The flower is preferably immature inflorescence.

The extract is preferably an ethanol extract.

The extract is preferably a hexane fraction or an ethyl acetate fraction of the ethanol extract.

Hereinafter, the preparation and efficacy assay of a hemp (Cannabis sativa L.) flower extract according to the present disclosure will be explained in detail.

The method for preparation and efficacy assay of a hemp (Cannabis sativa L.) flower extract according to the present disclosure comprises the steps of: preparing extracts from various parts of hemp through solvent extraction; evaluating the extracts for antithrombotic activity; fractioning the hemp flower extract with organic solvents sequentially; evaluating the fractions for antithrombotic activity; identifying the absence of THC in the ethyl acetate fraction; and examining safety and stability of the active fraction.

The "hemp flower extract" contained in the composition of the present disclosure may be obtained through the steps of preparing an extract from immature hemp flowers with an organic solvent, and filtering the extract solution through a filter with a pore size of 0.06 mm or less, followed by vacuum concentration.

The organic solvent used in the present disclosure may be water (cold or hot), hexane, methylene chloride, acetone, a liquor essence, an anhydrous or hydrated lower alcohol of 1-4 carbon atoms (methanol, ethanol, liquor essences, propanol, butanol, and so on), or a mixed solvent of the lower alcohol and water, with preference for hot water or 95% ethanol extraction.

In a particular embodiment, the hemp flower extract of the present disclosure may be an extract from an immature hemp flower. As used herein, the term "immature" is understood as pertaining to an inflorescence before seeds are borne. In addition, the flower is preferably not treated with heat additionally. Here, the ethanol extract may be fractioned with the organic solvents of hexane, ethyl acetate, and butanol, sequentially or separately, to obtain a hexane fraction, an ethyl acetate fraction, a butanol fraction, and a water residue additionally.

In the present disclosure, ethanol extracts were prepared from various parts of hemp, each adjusted into a concentration of 5 mg/ml, and measured for thrombin time, prothrombin time, and aPTT. From the measurements, it was found that all extracts from seeds, flowers, leaves, stems, and roots inhibit thrombus formation because they exhibited more potent inhibitory activity against thrombin and coagulation factors than 1.5 mg/ml aspirin does. The flower extract, unlike the other extracts, also exhibited more potent prothrombin inhibition than aspirin (1.5 mg/ml).

Unlike extracts from hemp leaves, stems, and roots, the hemp flow extract exhibited lytic activity on human erythrocytes. Hence, the flow extract was divided into an antithrombotic component and a hemolytic component. To this end, the flow extract was fractioned with organic solvents in a sequential manner to recover a hexane fraction and an ethyl acetate fraction which both have more potent antithrombotic activity, but are relatively poor in hemolytic activity. Particularly, an ethyl acetate fraction of the hemp flower extract is free of the addictive ingredient THC, and made each of the thrombin time and the aPTT 15-fold longer and the prothrombin time 2.62-fold longer at a concentration of 5 mg/ml than the non-added control. The ethanol extract of hemp flowers lysed erythrocytes by 98.3% at a concentration of 1 mg/ml while the ethyl acetate fraction of the hemp flower extract exhibited hemolysis by 34.8% at the same concentration. This hemolytic activity is similar to that of the potent anticancer agent amphotericin at a concentration of 0.006 mg/ml, implying that the fraction can be practically available. In addition, the fraction was found to be highly stable to heat and acid, so that the hemp flower extract and the ethyl acetate fraction thereof could be available in practice as agents for prevention or treatment/alleviation of thrombosis.

The hemp flower extract of the present disclosure may be prepared into powder through a typical powdering process such as vacuum drying and lyophilization or spray drying. The extract is not degraded by various enzymes in plasma and maintains activity even under the thermal treatment of 100° C. as well as at a pH of 2 in the human gastric environment.

The active ingredient of the present disclosure may be used for preventing or treating various thrombosis-related diseases. Examples of the diseases include arterial thrombosis, such as acute myocardial infarction, chest pain, dyspnea, loss of consciousness, ischemic stroke, hemorrhagic stroke, headache, motor abnormality, dysaesthesia, change of character, decreased vision, epileptic seizure, pulmonary thrombosis, deep vein thrombosis, lower limb edema, pain, and acute peripheral arterial obstruction, and venous thrombosis, such as deep vein thrombosis, portal vein thrombosis, acute renal vein obstruction, cerebral venous thrombosis, and subclavian vein obstruction.

A better understanding of the present disclosure may be obtained via the following examples which are set forth to illustrate, but are not to be construed as limiting the present disclosure.

EXAMPLES

Figure 2:
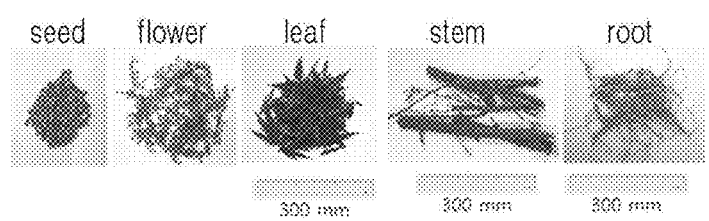
FIG. 2 shows photographic images of hemp parts used to prepare extracts, in which seeds, flowers (inflorescence), leaves, stems, and roots are arranged in the left to right direction.

Example 1: Preparation of Ethanol Extracts from Various Parts of Hemp and Analysis of Valuable Ingredient Thereof Hemp plants were seeded on April, 2020 in Andong city, Kyeongsangbuk-do, Korea, and immature hemp flowers (inflorescence), and matured hemp leaves, stems, roots, and seeds were harvested on October, 2020. The hemp seeds were husked and the bare seeds were used. For ethanol extract preparations, each material was added with 10 volumes of ethanol (95%, Duksan, Korea), followed by two rounds of extraction at room temperature. The extract solutions thus foiled were pooled, filtered, and concentrated at a reduced pressure to afford an ethanol extract as a powder. Photographic images of the hemp parts used are shown in FIG. 2. Extraction yields from various parts of hemp and analysis results of the valuable ingredients thereof are summarized in Table 1, below.

TABLE 1

Extraction Yield from Various Parts of Hemp and Analysis of Valuable Ingredients thereof

| Extract | Extraction yield(%) | Content (mg/g) | | |
|---|---|---|---|---|
| | | Total polyphenol | Total flavonoid | Total sugar |
| Seed | 12.9 | 7.5 ± 0.0 | 4.7 ± 0.1 | 51.5 ± 7.3 |
| Flower | 7.7 | 90.2 ± 5.5 | 38.0 ± 0.6 | 101.7 ± 0.9 |
| Leaf | 10.6 | 73.8 ± 0.1 | 32.9 ± 2.4 | 231.8 ± 14.0 |
| Stem | 3.5 | 31.5 ± 1.6 | 12.6 ± 0.2 | 230.6 ± 5.2 |
| Root | 5.9 | 41.9 ± 0.7 | 9.8 ± 0.1 | 173.7 ± 12.2 |

Extraction yields were in the order of stem<root<flower<leaf<seed, with 7.7% measured for the flower extraction yield. Hemp is one of the fastest growing plant on earth. Ingredients and extract yields may vary depending on maturity periods of hemp.

For valuable ingredient analysis by hemp part, the extracts were measured for total polyphenols, total flavonoids, and total sugars. A content of total polyphenols was determined by mixing 400 μl of a test liquid with 50 μl of Folin-Ciocalteau and 100 μl of $Na_2CO_3$ saturated solution, leaving the mixture at room temperature for 1 hour, and reading absorbance at 725 nm, with tannic acid serving as a standard reagent. For a content of total flavonoids, an extract was prepared by stirring each sample in methanol for 18 hours and 400 μl of a filtrate from the extract was added with 4 ml of 90% diethylene glycol and then with 40 μl of 1 N NaOH and reacted at 37° C. for 1 hour, followed by reading absorbance at 420 nm. Rutin was used as a standard reagent. Total sugars were quantitated using a phenol-sulfuric acid method, with sucrose serving as a standard reagent.

As shown in Table 1, the polyphenol content peaked at 90.2 mg/g from the flower extract while the lowest content was measured to be 7.5 mg/g in the seed extract. The polyphenol content was in the order of flower>leaf>root>stem>seed whereas the total flavonoid content was in the order of flower>leaf>stem>root>seed, with the peak at 38.0 mg/g in the flower extract. Thus, the hemp flower extract was identified to be richer in polyphenol and flavonoid substances than extracts from leaves, stems, roots, and seeds. The total sugar content was measured to be the highest from the leaf and stem extracts (ca. 230 mg/g), and the flower extract has a total sugar content of 101.7 mg/g, which was 40% of that of the root and stem extracts.

Example 2: Evaluation for Anticoagulant Activity of Extracts from Various Parts of Hemp Extracts from various parts of hemp in Example 1 were assayed for inhibitory activity against blood coagulation, and the results are summarized in Table 2. In this regard, the assay for anticoagulant activity of hemp extracts was conducted according to the methods reported previously (Sohn et al., 2004. Kor. J. Pharmacogn 35. 52-61; Kwon et al., 2004. J. Life Science, 14. 509-513; and Ryu, et al., 2010. J. Life Science, 20. 922-928) to evaluate thrombin time, prothrombin time, and aPTT. In this assay, commercially available control plasma (MD Pacific Technology Co., Ltd, Huayuan Industrial Area, China) was used, and tests for thrombin time, prothrombin time, and aPTT were carried out as follows.

Thrombin Time

At 37° C., 10 μl of each of sample extracts having various concentrations was mixed and reacted with 50 μl of 0.5 U thrombin (Sigma Co., USA) and 50 μl of 20 mM $CaCl_2$ for 2 min in an Amelung coagulometer KC-1A tube (Japan). After 100 μl of plasma was added to the mixture, the time it takes for a clot to form in the plasma was measured. As a control, aspirin (Sigma Co., USA) was used while DMSO, instead of the samples, served as a solvent control. For DMSO, the time taken to form a clot was 32.1 seconds. The thrombin time that accounts for a thrombin inhibition effect was expressed as a mean value of measurements from three or more independent experiments. Antithrombotic activity was explained by a ratio of the thrombin time in the presence of a sample to that in the presence of the solvent control.

Prothrombin Time

In an Amelung coagulometer KC-1A tube (Japan), 70 μl of standard plasma (MD Pacific Co., China) was heated, together with 10 μl of each of samples having various concentrations, at 37° C. for 3 min before adding 130 μl of PT reagent thereto. The time taken for a clot to form in the plasma was measured. This experiment was repeated three times independently. The prothrombin time was expressed as a mean value of the three measurements. As a control, aspirin (Sigma Co., USA) was used while DMSO, instead of the samples, served as a solvent control. For DMSO, the time taken to form a clot was 18.1 seconds. Anti-prothrombotic activity was explained by a ratio of the prothrombin time in the presence of a sample to that in the presence of the solvent control.

aPTT (activated Partial Thromboplastin Time)

In an Amelung coagulometer KC-1A tube (Japan), 10 μl of each of sample extracts having various concentrations was heated, together with 100 μl of plasma, at 37° C. for 3 min and added with 50 μl of aPTT reagent (Sigma, ALEXIN™), followed by incubation at 37° C. for 3 min, again. Subsequently, 50 μl of $CaCl_2$ (35 mM) was added. Then, the time it takes for a clot to form in the plasma was measured. Instead of samples, DMSO served as a solvent control. For DMSO, the time taken to form a clot was 55.1 seconds. The aPPT was expressed as a mean value of the measurements of three independent experiments. Blood coagulation factor inhibition activity was explained by a ratio of the aPPT in the presence of a sample to that in the presence of the solvent control.

TABLE 2

Blood Coagulation Inhibition Activity of Extracts from Various Parts of Hemp

| Control/Extract | Conc. (mg/ml) | Blood coagulation inhibition activity* | | |
|---|---|---|---|---|
| | | Thrombin Time | Prothrombin time | aPTT |
| Solvent control (DMS0) | | 1.00 ± 0.03 | 1.00 ± 0.01 | 1.00 ± 0.00 |
| Aspirin | 1.5 | 1.57 ± 0.06 | 1.42 ± 0.05 | 1.63 ± 0.03 |
| Seed | 5.0 | 2.00 ± 0.12 | 1.25 ± 0.04 | 1.36 ± 0.13 |
| Flower | 5.0 | 2.75 ± 0.02 | 1.80 ± 0.22 | 7.02 ± 0.59 |
| Leaf | 5.0 | 1.69 ± 0.08 | 1.22 ± 0.08 | 1.73 ± 0.11 |
| Stem | 5.0 | 2.31 ± 0.14 | 1.21 ± 0.06 | 1.55 ± 0.21 |
| Root | 5.0 | 2.04 ± 0.06 | 1.33 ± 0.02 | 1.88 ± 0.28 |

*Blood coagulation inhibition activity: time taken for a clot to form in sample added group/time taken for a clot to form in DMSO added group Thrombin time, prothrombin time, and aPTT measurements of extracts prepared from various parts of hemp, each having 5 mg/ml, are given in Table 2. As can be understood from the data, the most potent inhibitory activity against thrombin, prothrombin, and coagulation factors were detected from the flower extract which exhibited the thrombin time, the prothrombin time, and the aPTT prolonged by 2.75, 1.80, and 7.02 fold, respectively, compared to the non-added control and thus was superior in blood coagulation inhibition activity to aspirin (1.5 mg/ml) used as control, which prolonged the thrombin time, the prothrombin time, and the aPTT by 1.57, 1.42, and 1.63 fold, respectively. Thus, the hemp flower extract can effectively suppress blood coagulation by inhibiting various coagulation factors, thrombin, and prothrombin, finding applications as an alternative to aspirin with high side effects, such as gastrointestinal disorders.

Example 3: Human Erythrocyte Lysis Activity of Extracts from Various Parts of Hemp In herb medicine, hemp flowers, leaves, stems, roots, and seeds have been used as medicinal materials. In foreign countries, hemp leaves have been applied to foods and used as a therapeutic assistant for peripheral nerve injury (Aziz N. et al., 2019. Pak J Pharm Sci. 32 (Supplementary): 785-792) and thus are guaranteed safety for use in foods. However, objective evaluation for the safety of extracts from various hemp parts had not been made. Thus, the extracts were evaluated for acute toxicity in terms of human erythrocyte lysis.

In this regard, erythrocyte lysis activity was assayed as reported previously (Sohn, Ho-Yong, 2014. Korean J. Microbiol. Biotechnol. 42: 285-292). Briefly, 100 µl of human erythrocytes, after being washed three times with PBS, was added to each well of 96-well microplates, mixed with 100 µl of each of samples having various concentrations, and incubated at 37° C. for 30 min. Subsequently, the reaction mixture was centrifuged for 10 min (1,500 rpm). After 100 µl of the supernatant was transferred to new microtiter plates, absorbance was read at 414 nm to analyze hemoglobin release according to hemolysis. DMSO (2%) was used as a solvent control for the samples while Triton X-100 (1 mg/ml) served as a control for hemolysis. Hemolysis activity was calculated according to the following equation:

(%)Hemolysis=[(Abs. $S$–Abs. $C$)/(Abs. $T$–Abs. $C$)]×100

Abs. S: Absorbance of sample
Abs. C: Absorbance of DMSO
Abs. T: Absorbance of Triton X-100 added control

TABLE 3

Human Erythrocyte Lysis Activity of Extracts from Various Parts of Hemp

| Sample/Control | Conc. (mg/ml) | Human hemolytic activity (%) |
|---|---|---|
| Distilled water | — | 0.2 ± 0.3 |
| Solvent (DMSO) | — | 1.5 ± 1.1 |
| Triton X-100 | 1.0 | 100.6 ± 0.8 |
| Amphotericin B | 0.1 | 95.8 ± 0.3 |
| | 0.05 | 80.7 ± 7.3 |
| | 0.025 | 59.5 ± 6.3 |
| | 0.012 | 48.2 ± 5.9 |
| | 0.006 | 38.0 ± 0.7 |
| | 0.003 | 26.5 ± 9.6 |
| | 0 | 0.0 ± 0.2 |
| Seed | 1.0 | 90.1 ± 5.0 |
| Flower | 1.0 | 98.3 ± 0.2 |
| Leaf | 1.0 | 5.4 ± 9.0 |
| Stem | 1.0 | 2.8 ± 0.7 |
| Root | 1.0 | 2.1 ± 0.9 |

As shown in Table 3, no hemolysis was detected from the controls DMSO and water while Triton X-100 induced 100% hemolysis at a concentration of 1 mg/ml. In addition, amphotericin B, which is used as an anticancer agent and an antifungal agent, lysed erythrocytes by 50% or more at a concentration of 0.025 mg/ml.

On the other hand, the extracts from hemp leaves, stems, and roots were identified to be free of acute toxicity and hemolytic activity as none of them induced hemolysis at a concentration of up to 1 mg/ml. However, seed extracts exhibited the hemolytic activity of 90.1% at a concentration of 1 mg/ml and the flower extract exhibited the hemolytic activity of 98.3% at a concentration of 1 mg/ml. These results imply that it is necessary to remove a hemolytic component from the ethanol extract of hemp flowers according to the present disclosure.

Example 4: Preparation of Sequential Organic Solvent Fractions of Ethanol Extract from Hemp Flower and Ingredient Analysis The ethanol extract of hemp flowers, obtained in Example 3, having potent antithrombotic activity was fractionated with hexane, ethyl acetate, and butanol, sequentially, and water residues were finally recovered. Their fraction yields and ingredient analysis results are given in Table 4.

TABLE 4

Yield of Hemp Flower Extract and Fraction and Ingredient Analysis

| Hemp flower extract | Extraction/ Fraction yield (%) | Contents (mg/g) | | |
|---|---|---|---|---|
| | | Total polyphenol | Total flavonoid | Total sugar |
| Ethanol extract | 7.7 | 90.2 ± 5.5 | 38.0 ± 0.6 | 101.7 ± 0.9 |
| Hexane fraction | 37.0 | 44.3 ± 1.6 | 9.1 ± 0.3 | 35.7 ± 1.2 |

TABLE 4-continued

Yield of Hemp Flower Extract and
Fraction and Ingredient Analysis

| Hemp flower extract | Extraction/ Fraction yield (%) | Contents (mg/g) | | |
|---|---|---|---|---|
| | | Total polyphenol | Total flavonoid | Total sugar |
| Ethyl acetate fraction | 10.0 | 56.0 ± 5.2 | 36.8 ± 0.5 | 116.0 ± 2.0 |
| Butanol fraction | 52.5 | 39.3 ± 2.6 | 34.3 ± 0.8 | 275.6 ± 7.0 |
| Water residue | 0.5 | Not determined | Not determined | Not determined |

As shown in Table 4, the largest part in the sequential organic solvent fractions of the hemp flower extract was accounted for by the butanol fraction (52.5%) while the water residue was as low as 0.5% of the extract. The hexane fraction and the ethyl acetate fraction were yielded at 37.0% and 10.0% and recovered in an amount of 2.85 g and 0.77 g from 100 g of hemp flowers, respectively. As a result of analysis for total polyphenol and total flavonoid, the ethyl acetate fraction was the highest in polyphenol content (56.0 mg/g) and flavonoid content (36.8 mg/g) and a high polyphenol content (44.3 mg/g) was also detected from the hexane fraction. Therefore, the ethyl acetate fraction of the hemp flower extract was expected to have a variety of physiological activities. In practical analysis, the fraction was observed to have potent antioxidant activity and nitrite scavenging activity. An analysis result for total sugar showed that the sugars of the hemp flower extract were detected at a high level in the butanol fraction (153.2 mg/g) and measured to be 116.0 mg/g and 35.7 mg/g in the ethyl acetate fraction and the hexane fraction, respectively. Therefore, the ethyl acetate fraction of the hemp flower extract is understood to contain a large amount of polyphenolic glycosides, which were associated with sugars.

Example 5: Assay for Antithrombotic Activity of Sequential Organic Solvent Fractions of Ethanol Extract from Hemp Flower The fractions of hemp flower extract prepared in Example 4 were assayed for inhibitory activity against blood coagulation and the results are given in Table 5. In this regard, the inhibitory activity against blood coagulation was evaluated in the same manner as in Example 2.

TABLE 5

Blood Coagulation Inhibition Activity of Sequential
Organic Solvent Fractions of Hemp Flower Extract

| | Conc. (mg/ml) | Blood coagulation inhibition activity* | | |
|---|---|---|---|---|
| | | Thrombin Time | Prothrombin time | aPTT |
| DMSO | | 1.00 ± 0.04 | 1.00 ± 0.02 | 1.00 ± 0.05 |
| Aspirin | 1.5 | 1.44 ± 0.02 | 1.33 ± 0.08 | 1.64 ± 0.02 |
| Ethanol Extract | 7 | 3.06 ± 0.18 | 2.67 ± 0.13 | >15 |
| | 6 | 2.76 ± 0.01 | 2.09 ± 0.18 | >15 |
| | 5.0 | 2.75 ± 0.02 | 1.80 ± 0.22 | 7.02 ± 0.59 |
| Hexane fraction | 7.0 | >15 | >15 | >15 |
| | 6.0 | >15 | 6.14 ± 0.03 | >15 |
| | 5.0 | >15 | 2.85 ± 0.01 | 10.80 ± 0.19 |
| Ethyl acetate fraction | 7.0 | >15 | >15 | >15 |
| | 6.0 | >15 | 3.40 ± 0.12 | >15 |
| | 5.0 | >15 | 2.62 ± 0.05 | >15 |

TABLE 5-continued

Blood Coagulation Inhibition Activity of Sequential
Organic Solvent Fractions of Hemp Flower Extract

| | Conc. (mg/ml) | Blood coagulation inhibition activity* | | |
|---|---|---|---|---|
| | | Thrombin Time | Prothrombin time | aPTT |
| Butanol fraction | 7.0 | 2.10 ± 0.00 | 1.16 ± 0.05 | 2.33 ± 0.02 |
| | 6.0 | 1.83 ± 0.08 | 1.07 ± 0.03 | 2.08 ± 0.03 |
| | 5.0 | 1.7 ± 10.00 | 1.01 ± 0.11 | 1.69 ± 0.02 |

*Blood coagulation inhibition activity: time taken for a clot to form in sample added group/time taken for a clot to form in DMSO added group The ethanol extract from hemp flowers exhibited inhibitory activity against thrombin, prothrombin, and coagulation factors in a dose-dependent manner. Particularly, the aPTT, which is associated with intrinsic thrombus formation, was remarkably prolonged, demonstrating the antithrombotic activity of the hemp flower extract. Of the fractions of the ethanol extract, the hexane fraction and the ethyl acetate fraction each prolonged the thrombin time and the aPTT by 15 fold or greater at 5 mg/ml, compared to the non-added control, exhibiting potent inhibitory activity against intrinsic thrombus formation. The fractions inhibited prothrombin in a dose-dependent manner to extend the prothrombin time by 15 fold or greater at a concentration of 7 mg/ml, compared to the non-added control. In contrast, the butanol fraction which accounted for 52.5% of the ethanol fraction exhibited relatively weak antithrombotic activity. These data imply that the fractions of the ethanol extract from hemp flowers, the hexane fraction and the ethyl acetate fraction each have more potent antithrombotic activity than aspirin, which is used as an antithrombotic agent.

Example 6: Assay for Hemolytic Activity of Sequential Organic Solvent Fractions of Ethanol Extract from Hemp Flower The fractions of hemp flower extract prepared in Example 4 were assayed for hemolytic activity, and the results are given in Table 6. First, the hemp flower extract exhibited high hemolytic activity which was, however, no more than about 1/10 of that of the anticancer and antifungal agent amphotericin B, used as a control. Of the fractions, the hexane fraction lysed erythrocytes by as high as 80.1% at a concentration of 1.0 mg/ml and by 54.5% at a concentration of 0.5 mg/ml, showing hemolytic activity as large as about ½ that of the ethanol extract from hemp flowers. On the other hand, the ethyl acetate fraction lysed erythrocytes by 34.8% at a concentration of 1.0 mg/ml and by 6.3% at a concentration of 0.5 mg/ml, exhibiting negligible hemolytic activity compared to the ethanol extract from hemp flowers. The butanol fraction which accounted for 52.5% of the ethanol extract did not exhibit hemolysis at a concentration of up to 1.0 mg/ml. Having no acute toxicity, such as hemolysis in addition to exhibiting potent antithrombotic activity, the ethyl acetate fraction of the ethanol extract from hemp flowers could be available in practical applications.

TABLE 6

Lysis Activity on Human Erythrocyte of Sequential
Organic Solvent Fractions of Hemp Flower Extract

| Sample/Control | Conc. (mg/ml) | Human hemolytic activity (%) |
|---|---|---|
| Distilled water | — | 0.2 ± 0.3 |
| Solvent (DMSO) | — | 2.8 ± 2.1 |
| Triton X-100 | 1.0 | 100.6 ± 0.8 |
| Amphotericin B | 0.1 | 95.8 ± 0.3 |
|  | 0.05 | 80.7 ± 7.3 |
|  | 0.025 | 59.5 ± 6.3 |
|  | 0.0125 | 48.2 ± 5.9 |
|  | 0.00625 | 38.0 ± 0.7 |
|  | 0 | 0.0 ± 1.7 |
| Ethanol Extract | 1.0 | 98.3 ± 0.2 |
|  | 0.5 | 94.5 ± 0.8 |
|  | 0.25 | 60.1 ± 2.2 |
|  | 0.12 | 32.7 ± 6.7 |
|  | 0.06 | 2.9 ± 0.7 |
|  | 0.03 | 1.5 ± 0.5 |
| Hexane fraction | 1.0 | 80.1 ± 7.3 |
|  | 0.5 | 54.5 ± 0.9 |
| Ethyl acetate fraction | 1.0 | 34.8 ± 9.3 |
|  | 0.5 | 6.3 ± 2.8 |
| Butanol fraction | 1.0 | 1.0 ± 0.8 |
| Water residue | — | Not determined |

Example 7: Assay for Determining Presence or Absence of THC in Ethyl Acetate Fraction of Hemp Flower Extract The presence or absence of the addictive hallucinogen THC in the ethanol extract from hemp flowers and fractions thereof obtained in Example 4 was examined by thin layer chromatography (TLC) using the developing solvent of hexane:acetone (75:25 v/v) with Kieselgel 60F254 (Merck CO., Germany) serving as a support membrane. After development, the solvent was removed by heating and a 0.5% Fast blue B salt solution was applied to detect cannabinoids. As reference materials, THC and CBD were each used in an amount of 2 μg/spot. Test samples were an ethanol extract of hemp flowers and a hexane, an ethyl acetate, and a butanol fraction thereof, which were each dropwise added in an amount of 200 μg/spot.

Figure 3:
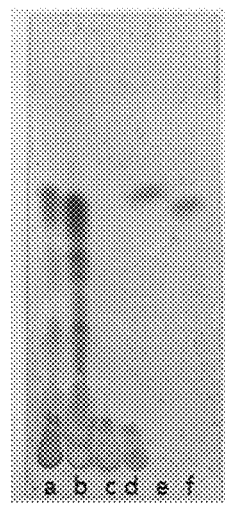
FIG. 3 shows a thin layer chromatogram of a hemp flower extract and fractions thereof: a: ethanol extract from hemp flower, b: hexane fraction of ethanol extract from hemp flower, c: ethyl acetate fraction of ethanol extract from hemp flower, d: butanol fraction of ethanol extract from hemp flower, e: tetrahydrocannabinol (THC) reference, and f: cannabidiol (CBD) reference.

As can be seen in FIG. 3, various cannabinoids including THC and CBD were detected in the ethanol extract of hemp flowers and the hexane fraction thereof. However, neither THC nor CBD were detected in the ethyl acetate fraction or butanol fraction of the ethanol extract from hemp flowers at all. In light of the report that the hallucinogen tetrahydrocannabinol, which is a main component of hemp flowers, has potent inhibitory activity against blood coagulation (Coetzee C et al., 2007. Phytomedicine. 14: 333-337), the results imply that the antithrombotic activity of the ethanol extract from hemp flowers and the hexane fraction thereof may come, in part, from THC while the potent antithrombotic activity of the ethyl acetate fraction is not attributed to already known cannabinoids such as THC, etc. Accordingly, the ethyl acetate active fraction of hemp flowers is highly available in practice because it does not possess the hallucinogen THC and exhibits potent antithrombotic activity.

Example 8: Assay for Plasma, Acid, and Heat Stability of Ethyl Acetate Fraction of Hemp Flower Extract The ethyl acetate fraction of the ethanol extract from hemp flower obtained in Example 4 was assayed for plasma, heat, and acid stability for blood clotting inhibition activity. Even after being treated at 100° C. for 1 hour, at pH 2 (0.01M HCl) for 1 hour, or in plasma for 1 hour, the fraction did not decrease in blood clotting inhibition activity. Thus, the active ethyl acetate fraction of hemp flowers was observed to contain an active antithrombotic entity stable to acid and heat and can be highly available in practice.

<3-Carene>

After extracts from various parts of hemp were identified to have potent antithrombotic activity, stem, leaf, and flower extracts were analyzed for various phenolic acid, flavonoids, and volatile ingredients. Antithrombotic activity of the hemp ingredient compounds thus obtained were evaluated. Finally, 3-carene was recovered as an entity of antithrombotic activity. 3-Carene has very low toxicity to the human body and is used as a food additive for flavoring or flavoring promotion in Europe and U.S.A. 3-Carene was identified to have stability to heat and acid and intended to be used in a method, pharmaceutical composition, and a health functional food for prevention or treatment/alleviation of thrombosis.

In brief, in order to develop a method, a pharmaceutical composition, and a health functional food for prevention or treatment/alleviation of thrombosis by using hemp, which is known in folk medicine to have advantageous effects on various diseases of blood vessels, the circulation system, the digestive system, and the metabolic system, various solvent extracts from hemp flowers, leaves, stems, roots, and seeds were prepared and assayed for antithrombotic activity in terms of direct thrombin inhibition against human thrombin (thrombin time), prothrombin inhibition (prothrombin time), and activated partial thromboplastin time (aPTT). From the assay, it was found that extracts from various parts of hemp have potent anticoagulant activity. Afterwards, an analysis result identified various phenolic ingredients, flavonoids, and aromatic ingredients in the extracts from various parts of hemp. The ingredients were evaluated for antithrombotic activity. As a result, 3-carene was finally found to be responsible for potent antithrombotic activity.

Therefore, the present disclosure provides a method for preventing or treating thrombosis, the method comprising administering a composition containing, as an active ingredient, 3-carene, which is a main volatile monoterpene found in hemp stems, leaves, and flowers.

The 3-carene may be preferably isolated from hemp stems, leaves, and flowers.

In addition, the present disclosure provides a composition and a health functional food comprising 3-carene as an active ingredient for prevention or alleviation of thrombosis.

The 3-carene may be preferably isolated from hemp stems, leaves, and flowers.

Hereinafter, the preparation and efficacy assay of 3-carene according to the present disclosure will be explained in detail.

The method for preparation and efficacy assay of 3-carene according to the present disclosure comprises the steps of: preparing extracts from various parts of hemp through solvent extraction; subjecting the extracts to GC-MS analysis; evaluating various polyphenols, flavonoids, and essential oils for antithrombotic activity; and examining safety and stability of 3-carene.

The "3-carene extract" contained in the composition of the present disclosure may be taken from basil, rosemary, bell pepper, pine trees, etc., but may be preferably isolated from hemp stems, leaves, and flowers. An ethanol extract is prepared from hemp stems, leaves, and flowers in a conventional manner and fractionated with hexane, followed by recovering 3-carene through gas-chromatography.

Figure 4:
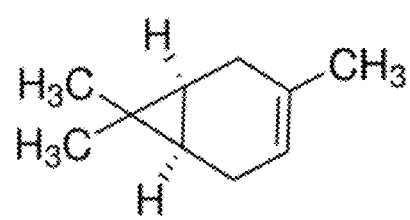
FIG. 4 is a structural formula of 3-carene.

3-Carene used in the present disclosure is represented by the structural formula of FIG. 4 and exists in a liquid phase at room temperature, with a molecular weight of 136, a specific gravity of 0.86 g/ml, and a boiling point of 172° C., and is colorless and not soluble in water, but miscible with oil.

The 3-carene of the present disclosure may be used for preventing or treating various thrombosis-related diseases. Examples of the diseases include arterial thrombosis, such as acute myocardial infarction, chest pain, dyspnea, loss of consciousness, ischemic stroke, hemorrhagic stroke, headache, motor abnormality, dysaesthesia, change of character, decreased vision, epileptic seizure, pulmonary thrombosis, deep vein thrombosis, lower limb edema, pain, and acute peripheral arterial obstruction, and venous thrombosis, such as deep vein thrombosis, portal vein thrombosis, acute renal vein obstruction, cerebral venous thrombosis, and subclavian vein obstruction.

A better understanding of the present disclosure may be obtained via the following examples which are set forth to illustrate, but are not to be construed as limiting the present disclosure.

EXAMPLES

Example 1: GC/MS Analysis of Essential Oils in Hemp Stem

Figure 5:
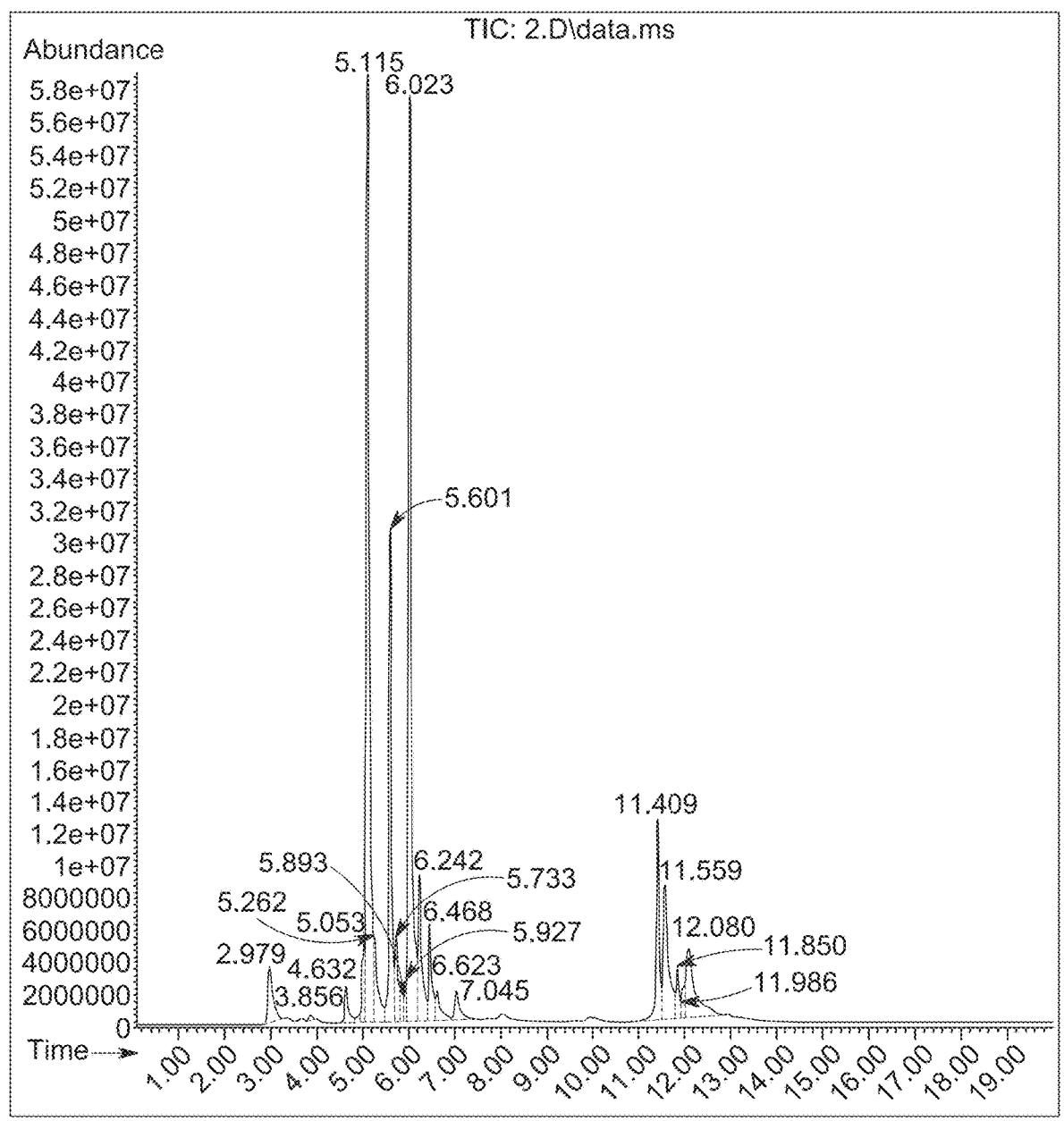
FIG. 5 is a GC/MS (Gas Chromatography/Mass Spectrometer) spectrum of ingredients in hemp stems.

After hemp plants were seeded on April, 2020 in Andong city, Kyeongsangbuk-do, Korea, a harvest was made of hemp leaves and stems on September, 2020 and of flowers on October, 2020. The hemp leaves, stems, and flowers were analyzed for volatile ingredients. The GC/MS was equipped with Liquid & Headspace autosampler. A sample was injected into the GC (7890, Agilent) analysis column HP-5MS (30 m, 0.25 mm×0.25 μm) and MS (Agilent 5975C) was operated in an EI mode. The injector inlet was set to be 280° C. while the column oven temperature was programed as follows: the initial temperature was 80° C. and kept for 5 min and increased to up to 250° C. at a rate of 5° C./min and then reached a final temperature of 320° C. from 250° C. at a rate of 10° C./min. Helium gas was used as a mobile phase with a flow rate of 1 ml/min. Injection was made in a 10:1 split mode. The GC-MS data thus obtained were analyzed in comparison with MS library data (NIST). Analysis results of representative volatile ingredients in hemp stems are given in FIG. 5 and Table 1, below.

As can be seen from the data, most of the total volatile essential oils are accounted for by carenes, with 3-carene and (+)-4-carene occupying 27.28% and 25.96%, respectively.

TABLE 1

Analysis of Volatile Ingredient in Hemp Stem

| Compound | Relative content (%) |
| --- | --- |
| Dimethyl sulfide | 2.25 |
| Hexanal | 0.18 |
| Bicyclo[4.2.0]octa-1,3,5-triene | 1.13 |
| .alpha.-Phellandrene | 1.38 |
| (+)-4-Carene | 25.96 |
| 3-Carene | 27.28 |
| Bicyclo[3.1.1]heptane,6,6-dimethyl-2-methylene-,(1S)- | 10.68 |

TABLE 1-continued

Analysis of Volatile Ingredient in Hemp Stem

| Compound | Relative content (%) |
| --- | --- |
| .beta.-Pinene | 1.98 |
| .beta.-Pinene | 0.37 |
| Bicyclo[3.1.0]hex-2-ene, 2-methyl-5-(1-methylethyl)- | 0.62 |
| .gamma.-Terpinene | 4.26 |
| 1,3,6-Octatriene, 3,7-dimethyl-, (Z)- | 2.57 |
| .gamma.-Terpinene | 1.14 |
| Cyclohexene, 1-methyl-4-(1-methylethylidene)- | 1.26 |
| Alloaromadendrene | 5.50 |
| Caryophyllene | 6.02 |
| Alloaromadendrene | 1.44 |
| Humulene | 0.75 |
| Aromandendrene | 4.93 |

Example 2: UPLC/MS/MS Analysis of Phenolic Acid and Flavonoid in Hemp Stem

Ethanol extracts from various hemp parts were analyzed for phenolic acids and flavonoids. For ethanol extract preparation, each material was added with 10 volumes of ethanol (95%, Duksan, Korea), followed by two rounds of extraction at room temperature. The extract solutions thus formed were pooled, filtered, and concentrated at a reduced pressure to afford an ethanol extract as a powder. Extracts from various hemp parts were analyzed using UPLC (Acquity i class, Waters, Milford, USA)/MS/MS (TSQ Quantum ULTRA, Thermo Fisher, Waltham, USA). As reference substances, a total of 13 phenolic acids including caffeic acid, cinnamic acid, ρ-coumaric acid, m-coumaric acid, ferulic acid, gallic acid, gentisic acid, 4-hydroxybenzoic acid, protocatechuic acid, salicylic acid, sinapic acid, syringic acid, and vanillic acid, and a total of 14 flavonoids including apiin, astragalin, cosmosiin, fisetin, hyperoside, isoquercitrin, kaempferol, luteolin, myricetin, orientin, quercetin, quercitrin, rutin, and vitexin, all commercially available from Sigma Co. (St. Louis, Mo., USA), were used. UPLC analysis conditions were as follows: 1.7 μm column from ACQUITY UPLC® BEH C18; column temperature, 40° C.; flow rate, 350 μl/min; injection amount, 2 μl; mobile solvent, gradient elution with 0.1% formic acid in distilled water and 0.1% formic acid in acetonitrile. MS/MS analysis was performed in the multiple reaction monitoring (MRM) mode for enhancing selectivity and detection sensitivity by selecting the hydrogenated molecular ions ([M-H]$^-$) as precursor ions for each ingredient. Through tuning work, optimal collision energy and product ions were selected. MS analysis was carried out in the negative ionization mode which works under the following conditions: spray voltage 2.0 kV, desolvation gas flow rate 800 L/hr, cone gas flow rate 1 L/hr, and desolvation temperature 450° C.

For orientin, the analysis was performed in the positive ionization mode. All the mobile solvents employed were of HPLC/MS/MS grade.

TABLE 2

Phenolic Acid and Flavonoid Ingredient Analysis of Hemp Stem

| | Compound | Relative content (%) |
| --- | --- | --- |
| Flavonoid | Cosmosin(ng/mL) | 3.61 |
| | Fisetin(ng/mL) | 0 |
| | Kaempferol(ng/mL) | 29.13 |

TABLE 2-continued

Phenolic Acid and Flavonoid Ingredient Analysis of Hemp Stem

| | Compound | Relative content (%) |
|---|---|---|
| | Liteolin(ng/mL) | 12.68 |
| | Myricetin(ng/mL) | 26.66 |
| | Quercetin(ng/mL) | 0 |
| | Quercitrin(ng/mL) | 0 |
| | Vitexin(ng/mL) | 0 |
| | Galangin(ng/mL) | 70.73 |
| | Hyperoside(ng/mL) | 8.34 |
| | Hesperidin(ng/mL) | 6.79 |
| Phenolic acid | 4-Hydroxybenzoic acid(ng/mL) | 241.28 |
| | Syringic acid(ng/mL) | 10.46 |
| | Sinapic acid(ng/mL) | 7.01 |
| | Salicylic acid(ng/mL) | 0 |
| | Protocatechuic acid(ng/mL) | 15.38 |
| | p-Coumaric acid(ng/mL) | 7.79 |
| | m-Coumaric acid(ng/mL) | 0 |
| | Gentisic acid(ng/mL) | 10.81 |
| | Gallic acid(ng/mL) | 9.97 |
| | Ferulic acid(ng/mL) | 6.79 |
| | Caffeic acid(ng/mL) | 9.45 |

As shown in Table 2, hemp stems were found to contain 4-hydroxybenzoic acid (241.28 ng/mL), protocatechuic acid (15.38 ng/mL), and gentisic acid (10.81 ng/mL) as main phenolic acids and galangin (70.73 ng/mL), kaempferol (29.13 ng/mL), and myricetin (26.66 ng/mL) as main flavonoids.

Example 3: Evaluation for Antithrombotic Activity of 3-Carene

As a result of antithrombotic activity assay, 3-carene was identified to have the most potent anticoagulant activity among various compounds derived by hemp in Examples 1 and 2. The antithrombotic activity assay results are summarized in Table 3, below. In this regard, the assay for anticoagulant activity of various compounds derived from hemp was conducted according to the methods reported previously (Sohn et al., 2004. Kor. J. Pharmacogn 35. 52-61; Kwon et al., 2004. J. Life Science, 14. 509-513; and Ryu, et al., 2010. J. Life Science, 20. 922-928) to evaluate thrombin time, prothrombin time, and aPTT. In this assay, commercially available control plasma (MD Pacific Technology Co., Ltd, Huayuan Industrial Area, China) was used, and tests for thrombin time, prothrombin time, and aPTT were carried out as follows.

Thrombin Time

At 37° C., 10 µl of each of sample extracts having various concentrations was mixed and reacted with 50 µl of 0.5 U thrombin (Sigma Co., USA) and 50 µl of 20 mM $CaCl_2$ for 2 min in an Amelung coagulometer KC-1A tube (Japan). After 100 µl of plasma was added to the mixture, the time it takes for a clot to form in the plasma was measured. As a control, aspirin (Sigma Co., USA) was used while DMSO, instead of the samples, served as a solvent control. For DMSO, the time taken to form a clot was 32.1 seconds. The thrombin time that accounts for a thrombin inhibition effect was expressed as a mean value of measurements from three or more independent experiments. Antithrombotic activity was explained by a ratio of the thrombin time in the presence of a sample to that in the presence of the solvent control.

Prothrombin Time

In an Amelung coagulometer KC-1A tube (Japan), 70 µl of standard plasma (MD Pacific Co., China) was heated, together with 10 µl of each of samples having various concentrations, at 37° C. for 3 min before adding 130 µl of PT reagent thereto. The time taken for a clot to form in the plasma was measured. This experiment was repeated three times independently. The prothrombin time was expressed as a mean value of the three measurements. As a control, aspirin (Sigma Co., USA) was used while DMSO, instead of the samples, served as a solvent control. For DMSO, the time taken to form a clot was 18.1 seconds. Anti-prothrombotic activity was explained by a ratio of the prothrombin time in the presence of a sample to that in the presence of the solvent control.

aPTT (activated Partial Thromboplastin Time)

In an Amelung coagulometer KC-1A tube (Japan), 10 µl of each of sample extracts having various concentrations was heated, together with 100 µl of plasma, at 37° C. for 3 min and added with 50 µl of aPTT reagent (Sigma, ALEXIN™), followed by incubation at 37° C. for 3 min, again Subsequently, 50 µl of $CaCl_2$ (35 mM) was added. Then, the time it takes for a clot to form in the plasma was measured. Instead of samples, DMSO served as a solvent control. For DMSO, the time taken to form a clot was 55.1 seconds. The aPPT was expressed as a mean value of the measurements of three independent experiments. Blood coagulation factor inhibition activity was explained by a ratio of the aPPT in the presence of a sample to that in the presence of the solvent control.

TABLE 3

Blood Coagulation Inhibition Activity of 3-Carene

| | | Blood coagulation inhibition activity* | | |
|---|---|---|---|---|
| Control/Extract | Conc. (mg/ml) | Thrombin Time | Prothrombin Time | aPTT |
| Solvent control (DMSO) | | 1.00 ± 0.03 | 1.00 ± 0.01 | 1.00 ± 0.02 |
| Aspirin | 1.5 | 1.46 ± 0.01 | 1.38 ± 0.02 | 1.52 ± 0.04 |
| 3-Carene | 1.0 | 2.55 ± 0.00 | 1.43 ± 0.09 | 2.26 ± 0.08 |
| | 0.75 | 2.14 ± 0.13 | 1.29 ± 0.00 | 1.61 ± 0.03 |
| | 0.5 | 1.56 ± 0.01 | 1.05 ± 0.02 | 1.23 ± 0.05 |
| 4-Hydroxybenzoic acid | 0.5 | 1.34 ± 0.04 | 0.99 ± 0.00 | 0.94 ± 0.15 |
| Vitexin | 0.5 | 1.40 ± 0.00 | 0.98 ± 0.02 | 1.00 ± 0.10 |

*Blood coagulation inhibition activity: time taken for a clot to form in sample added group/time taken for a clot to form in DMSO added group As shown in Table 3, 3-carene effectively prevented blood clotting even at a concentration of as low as 0.5 mg/ml through excellent inhibitory activity against thrombin and coagulation factors, which is superior to the conventional anticoagulants 4-hydroxybenzoic acid and Vitexin in terms of anticoagulant activity (Kim M S, 2016. J. Microbiol. Biotechnol. 26: 61-65; Song, S J. 2012. Plant Med. 78: 1967-1971). Particularly, 3-carene inhibited thrombus formation in a dose-dependent manner. At a concentration of 1 mg/ml, 3-carene prolonged the thrombin time by 2.55 fold, the prothrombin time by 1.43 fold, the aPTT by 2.26 fold, compared to the non-added control and thus was more potent in anticoagulant activity than the anticoagulant aspirin at a concentration of 1.5 mg/ml. Therefore, 3-carene can effectively prevent thrombus formation through inhibitory activity against thrombin, prothrombin, and various coagulation factors which are all involved in intrinsic and extrinsic blood clotting and could serve as an alternative to conventional antiplatelet agent with high side effects, such as aspirin.

As described hitherto, the hemp (*Cannabis sativa* L.) leaf or flower extract inhibits thrombus formation-related enzymes and coagulation factors and exhibits potent antithrombotic activity through inhibitory activity against platelet aggregation which triggers blood clotting, but with no lytic activity on human erythrocytes. In addition to being stable to heat, the extract does not lose the inhibitory activity against coagulation factors and thrombus formation-related enzymes even in the acidic condition of pH 2 and the plasma environment. Therefore, the extract is expected to find applications in preventing and treating thrombosis such as ischemic stroke and hemorrhagic stroke through blood circulation improvement. Moreover, the active ingredient may be processed into various forms such as a solution, a powder, a pill, a tablet, and so on, and can be administered at any time. Accordingly, the present disclosure is very advantageous for the pharmaceutical and food industries.

What is claimed is:

1. A method for treating thrombosis in a human in need thereof consisting essentially of administering to the human in need thereof an immature inflorescene ethanol hemp flower extract.

2. The method of claim 1, wherein the extract consists essentially of 3-carene.

\* \* \* \* \*